United States Patent [19]

Morikawa et al.

[11] Patent Number: 5,545,777
[45] Date of Patent: Aug. 13, 1996

[54] PROCESS FOR PRODUCING A HYDROGEN-CONTAINING 2,2-DIFLUOROPROPANE

[75] Inventors: Shinsuke Morikawa, Yokohama; Shunichi Samejima, Tokyo; Masaru Yoshitake, Yokohama; Hidekazu Okamoto, Yokohama; Keiichi Ohnishi, Yokohama; Toshihiro Tanuma, Yokohama, all of Japan

[73] Assignee: Asahi Glass Company Ltd., Tokyo, Japan

[21] Appl. No.: 272,622

[22] Filed: Jul. 11, 1994

Related U.S. Application Data

[63] Continuation of Ser. No. 968,247, Oct. 30, 1992, abandoned, which is a continuation of Ser. No. 857,118, Mar. 25, 1992, abandoned, which is a continuation of Ser. No. 573,121, filed as PCT/JP90/00122, Feb. 1, 1990, abandoned.

[30] Foreign Application Priority Data

| Feb. 2, 1989 | [JP] | Japan | 1-22542 |
| Feb. 2, 1989 | [JP] | Japan | 1-22624 |
| Feb. 3, 1989 | [JP] | Japan | 1-23746 |
| Feb. 3, 1989 | [JP] | Japan | 1-23747 |
| Feb. 3, 1989 | [JP] | Japan | 1-23748 |
| Feb. 3, 1989 | [JP] | Japan | 1-23749 |

[51] Int. Cl.⁶ .................................................. C07C 19/08
[52] U.S. Cl. ........................................................ 570/176
[58] Field of Search .................................................. 570/176

[56] References Cited

U.S. PATENT DOCUMENTS

| 2,494,064 | 1/1950 | Simons et al. | |
| 2,920,112 | 1/1960 | Larsen | 570/176 |
| 4,745,237 | 5/1988 | Ballard et al. | 570/176 |
| 5,264,639 | 11/1993 | Morikawa et al. | |

FOREIGN PATENT DOCUMENTS

| 0347830 | 12/1989 | European Pat. Off. | 570/176 |
| 1177853 | 1/1970 | United Kingdom . | |
| 1578933 | 5/1977 | United Kingdom . | |

OTHER PUBLICATIONS

Georg Thieme Verlag–Stuttgart, vol. V/4, pp. 762–768, 1960, Methoden Der Organischen Chemie, Eugen Muller.

Houben–Weil: "Methoden der Organischen Chemie", 4th edition, vol. V/4, "Halogenverbindungen", 1960, Georg Thieme Verlag (Stuttgart, DE), pp. 762–768.

*Primary Examiner*—Alan Siegel
*Attorney, Agent, or Firm*—Oblon, Spivak, McClelland, Maier & Neustadt, P.C.

[57] ABSTRACT

A process for producing a hydrogen-containing 2,2-difluoropropane of the following formula (2), which comprises subjecting a 2,2-difluoropropane of the following formula (1) to hydrogen reduction:

$$C_3H_aCl_bF_c \qquad (1)$$

$$C_3H_{a+x}Cl_{b-y}F_{c-z} \qquad (2)$$

wherein a, b, c, x, y and z are integers satisfying the following conditions:
$a \geq 0$, $b \geq 1$, $c \geq 2$, $x \geq 1$, $y \geq 0$, $z \geq 0$, $a+b+c=8$, $x=y+z$ $b-y \geq 0$, and $c-z \geq 2$.

2 Claims, No Drawings

PROCESS FOR PRODUCING A HYDROGEN-CONTAINING 2,2-DIFLUOROPROPANE

This application is a Continuation of application Ser. No. 07/968,247 filed on Oct. 30, 1992, abandoned, which is a continuation of 07/857,118 which was filed on Mar. 25, 1992, abandoned, which is a continuation 07/573,121 which was filed on Sep. 13, 1990, abandoned, which was filed as International Application No. PCT/JP90/00122 on Feb. 1, 1990.

TECHNICAL FIELD

The present Invention relates to a process for producing a hydrogen-containing 2,2-difluoropropane.

BACKGROUND TECHNIQUE

As a synthetic route for a hydrogen-containing 2,2-difluoropropane, a method has been known wherein trichloromethane or the like is added to an ethylene having a difluoromethylene unit, such as 1,1-dichloro-2,2-difluoroethylene in the presence of aluminum chloride. However, by this method, not only the desired product but also a by-product which has a methylene group other than 2,2-difluoroethylene and which has a boiling point close to that of the desired product, is likely to be formed. Thus, it has a drawback that in order to obtain a product with a high purity, a multi-stage purification process is required.

DISCLOSURE OF THE INVENTION

It is an object of the present invention to overcome such a drawback and to provide a process for efficiently producing a hydrogen-containing 2,2-difluoropropane.

The present inventors have conducted an extensive research for a process for efficiently producing a hydrogen-containing 2,2-difluoropropane and as a result, have found it possible to obtain a hydrogen-containing 2,2-difluoropropane or the following formula (2) in good yield by subjecting a 2,2-difluoropropane of the formula (1) to hydrogen reduction. The present invention has been accomplished on the basis of this discovery.

The present invention provides a process for producing a hydrogen-containing 2,2-difluoropropane of the following formula (2), which comprises subjecting a 2,2-difluoropropane of the following formula (1) to hydrogen reduction:

$$C_3H_aCl_bF_c \quad (1)$$

$$C_3H_{a+x}Cl_{b-y}F_{c-z} \quad (2)$$

wherein a, b, c, x, y and z are integers satisfying the following conditions:

$a\geq 0$, $b\geq 1$, $c\geq 2$, $x\geq 1$, $y\geq 0$, $z\geq 0$, $a+b+c=8$, $x=y+z$
$b-y\geq 0$, and $c-z\geq 2$.

The hydrogen-containing 2,2-difluoropropane is expected to be useful as a foaming agent, a cooling medium, a propellant or a solvent like conventional chlorofluorocarbons. Particularly, it is a promising substitute for 1,1,2-trichlorotrifluoroethane as a solvent.

BEST MODE FOR CARRYING OUT THE INVENTION

Reactions of the following formulas (3) to (7) may be mentioned as specific embodiments of the reaction to obtain of the product of the formula (2) by hydrogen reduction of the starting material of the formula (1).

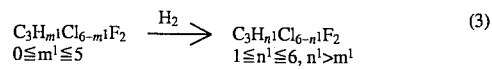

The 2,2-difluoropropane ($C_3H_{m^1}Cl_{6-m^1}F_2$ wherein $0\geq m^1\geq 5$) to be used as the starting material includes 1,1,1,3,3,3-hexachloro-2,2-difluoropropane (R-212ca), 1,1,1,3,3-pentachloro-2,2-difluoropropane (R-222ca), 1,1,3,3-tetrachloro-2,2-difluoropropane (R-232ca), 1,1,1,3tetrachloro-2,2,-difluoropropane (R-232cb), 1,1,3-trichloro-2,2-difluoropropane (R-242ca), 1,1,1-trichloro-2,2-difluoropropane (R-242cb), 1,3-dichloro-2,2-difluoropropane (R-252ca), 1,1-dichloro-2,2-difluoropropane (R-252cb) and 1-chloro-2,2-difluoropropane (R-262ca).

The hydrogen-containing 2,2-difluoropropane ($C_3H_{n^1}Cl_{6-n^1}F_2$ wherein $1\geq n^1\geq 6$) to be formed by the reaction includes 1,1,1,3,3-pentachloro-2,2-difluoropropane (R-222ca), 1,1,3,3-tetrachloro-2,2-difluoropropane (R-232ca), 1,1,1,3-tetrachloro-2,2-difluoropropane (R-232cb), 1,1,3-trichloro-2,2-difluoropropane (R-242ca), 1,1,1-trichloro-2,2-difluoropropane (R-242cb), 1,3-dichloro-2,2-difluoropropane (R-252ca), 1,1-dichloro-2,2-difluoropropane (R-252ca), 1-chloro-2,2-difluoropropane (R-262ca) and 2,2-difluoropropane (R-272ca). These products can be separated by a usual method such as distillation.

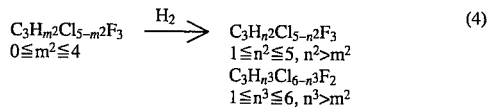

The 2,2-difluoropropane ($C_3H_{m^2}Cl_{5-m^2}F_3$ wherein $0\geq m^2\geq 4$) to be used as the starting material includes 1,1,1,3,3-pentachloro-2,2,3-trifluoropropane (R-213c), 1,1,1,3-tetrachloro-2,2,3-trifluoropropane (R-223cb), 1,1,3,3-tetrachloro-1,2,2-trifluoropropane (R-223ca), 1,1,3-trichloro-1,2,2-trifluoropropane (R-233cb), 1,1-dichloro-1,2,2-trifluoropropane (R-243cc), 1,1-dichloro-2,2,3-trifluoropropane (R-243cb), 1,3-dichloro-1,2,2-trifluoropropane (R-243ca), 1-chloro-1,2,2-trifluoropropane (R-254cb) and 1-chloro-2,2,3-trifluoropropane (R-253ca).

The hydrogen-containing 2,2-difluoropropane ($C_3H_{n^2}Cl_{5-n^2}F_3$ wherein $1\geq n^2\geq 5$) to be formed by the reaction includes 1,1,1,3-tetrachloro-2,2,3-trifluoropropane (R-223cb), 1,1,3,3-tetrachloro-1,2,2-trifluoropropane (R-223ca), 1,1,1-trichloro-2,2,3-trifluoropropane (R-233cc), 1,1,3-trichloro-1,2,2-trifluoropropane (R-233cb), 1,1,3-trichloro-2,2,3-trifluoropropane (R-233ca), 1,1-dichloro-1,2,2-trifluoropropane (R-243cc), 1,1-dichloro-2,2,3-trifluoropropane (R-243cb), 1,3-dichloro-1,2,2-trifluoropropane (R-243ca), 1-chloro-1,2,2-trifluoropropane (R-253cb), 1-chloro-2,2,3-trifluoropropane (R-253ca), 1,2,2-trifluoropropane (R-263c). Likewise, the hydrogen-containing 2,2-difluoropropane ($C_3H_{n^3}Cl_{6-n^3}F_2$ wherein $1\geq n^3\geq 6$) includes 1,1,3-trichloro-2,2-difluoropropane (R-242cb), 1,1-dichloro-2,2-difluoropropane (R-252cb) and 1-chloro-2,2-difluoropropane (R-262c). These products can be separated by a usual method such as distillation.

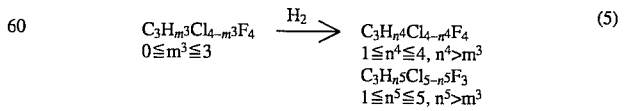

The 2,2-difluoropropane ($C_3H_{m^3}Cl_{4-m^3}F_4$ wherein $0\geq m^3\geq 3$) to be used as the starting material includes 1,1,3,3-tetrachloro-1,2,2,3-tetrafluoropropane (R-214ca), 1,1,1,3-tetrachloro-2,2,3,3-tetrafluoropropane (R-214cb), 1,1,3-trichloro-2,2,3,3-tetrafluoropropane (R-224ca), 1,1,3-trichloro-1,2,2,3-tetrafluoropropane (R-224cb), 1,1,1-trichloro-2,2,3,3-tetrafluoropropane (R-224cc), 1,3-dichloro-1,2,2,3-tetrafluoropropane (R-234ca), 1,1-dichloro-2,2,3,3-tetrafluoropropane (R-234cb), 1,3-dichloro-1,1,2,2-tetrafluoropropane (R-234cc), 1,1-dichloro-1,2,2,3-tetrafluoropropane (R-234cd), 1-chloro-2,2,3,3-tetrafluoropropane (R-244ca), 1-chloro-1,2,2,3-tetrafluoropropane (R-244cb) and 1-chloro-1,1,2,2-tetrafluoropropane (R-244cc).

The hydrogen-containing 2,2-difluoropropane ($C_3H_{n^4}Cl_{4-n^4}F_4$ wherein $1 \geq n^4 \geq 4$) to be formed by the reaction includes 1,1,3-trichloro-2,2,3,3-tetrafluoropropane (R-224ca), 1,1,3-trichloro-1,2,2,3-tetrafluoropropane (R-224cb), 1,1,1-trichloro-2,2,3,3-tetrafluoropropane (R-224cc), 1,3-dichloro-1,2,2,3-tetrafluoropropane (R-234ca), 1,1-dichloro-2,2,3,3-tetrafluoropropane (R-234cb), 1,3-dichloro-1,1,2,2-tetrafluoropropane (R-234cc), 1,1-dichloro-1,2,2,3-tetrafluoropropane (R-234cd), 1-chloro-2,2,3,3-tetrafluoropropane (R-244ca), 1-chloro-1,2,2,3-tetrafluoropropane (R-244cb), 1-chloro-1,1,2,2-tetrafluoropropane (R-244cc), 1,2,2,3-tetrafluoropropane (R-254ca) and 1,1,2,2-tetrafluoropropane (R-254cb). Likewise, the hydrogen-containing 2,2-difluoropropane ($C_3H_{n^5}Cl_{5-n^5}F_3$ wherein $1 \geq n^5 \geq 5$) includes 1,1-dichloro-1,2,2-trifluoropropane (R-243cc), 1-chloro-1,2,2-trifluoropropane (R-254cb) and 1,2,2-trifluoropropane (R-263ca). These products can be separated by a usual method such as distillation.

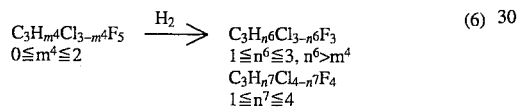

(6)

The 2,2-difluoropropane ($C_3H_{m^4}Cl_{3-m^4}F_5$ wherein $0 \geq m^4 \geq 2$) having a difluoromethylene group to be used as the starting material includes 1,1,3-trichloro-1,2,2,3,3-pentafluoropropane (R-215ca), 1,1,1-trichloro-2,2,3,3,3-pentafluoropropane (R-215cb), 1,1-dichloro-2,2,3,3,3-pentafluoropropane (R-225ca), 1,3-dichloro-1,1,2,2,3-pentafluoropropane (R-225cb), 1,1-dichloro-1,2,2,3,3-pentafluoropropane (R-225cb), 1-chloro-1,2,2,3,3-pentafluoropropane (R-235ca), 1-chloro-2,2,3,3,3-pentafluoropropane (R-235cb) and 1-chloro-1,1,2,2,3-pentafluoropropane (R-235cc).

The hydrogen-containing 2,2-difluoropropane ($C_3H_{n^6}Cl_{3-n^6}F_5$ wherein $1 \geq n^6 \geq 3$) to be formed by the reaction includes 1,1-dichloro-2,2,3,3,3-pentafluoropropane (R-225ca), 1,3-dichloro-1,1,2,2,3-pentafluoropropane (R-225cb), 1,1-dichloro-1,2,2,3,3-pentafluoropropane (R-225cc), 1-chloro-1,2,2,3,3-pentafluoropropane (R-235ca), 1-chloro-2,2,3,3,3-pentafluoropropane (R-235cb), 1-chloro-1,1,2,2,3-pentafluoropropane (R-235cc), 1,1,2,2,3-pentafluoropropane (R-245ca) and 1,1,1,2,2-pentafluoropropane (R-245cb). Likewise, the hydrogen-containing 2,2-difluoropropane ($C_3H_{n^7}Cl_{4-n^7}F_4$ wherein $1 \geq n^7 \geq 4$) includes 1-chloro-1,1,2,2-tetrafluoropropane (R-244cc) and 1,1,2,2-tetrafluoropropane (R-254cb). These products can be separated by a usual method such as distillation.

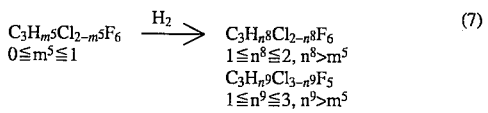

(7)

The 2,2-difluoropropane ($C_3H_{m^5}Cl_{2-m^5}F_6$ wherein $0 \geq m^5 \geq 1$) to be used as the starting material includes 1,3-dichloro-1,1,2,2,3,3-hexafluoropropane (R-216ca), 1,1-dichloro-1,2,2,3,3,3-hexafluoropropane (R-216cb), 1-chloro-1,2,2,3,3,3-hexafluoropropane (R-226ca) and 1-chloro-1,1,2,2,3,3-hexafluoropropane (R-226cb).

The hydrogen-containing 2,2-difluoropropane ($C_3H_{n^8}Cl_{2-n^8}F_6$ wherein $1 \geq n^8 \geq 2$) to be formed by the reaction includes 1-chloro-1,2,2,3,3,3-hexafluoropropane (R-226ca), 1-chloro-1,1,2,2,3,3-hexafluoropropane (R-226cb), 1,1,2,2,3,3-hexafluoropropane (R-236ca) and 1,1,1,2,2,3-hexafluoropropane (R-236cb). Likewise, the hydrogen-containing 2,2-difluoropropane ($C_3H_{n^9}Cl_{3-n^9}F_5$ wherein $1 \geq n^9 \geq 3$) includes 1,1,1,2,2-pentafluoropropane (R-245cb). These products can be separated by a usual method such as distillation.

In the present invention, the hydrogen reduction is preferably conducted by reacting the starting material with a combination of zinc and a hydrogen-forming agent or with hydrogen in the presence of a hydrogenation catalyst.

As the hydrogen-forming agent, a protonic solvent is preferred. There is no particular restriction as to the protonic solvent. However, a lower alcohol such as methanol, ethanol or isopropyl alcohol, water or acetic acid is preferred. Among them, methanol is particularly suitable.

The zinc to be used in the present invention may be in any form such as a powder, granules or fragments. However, it is most preferred to employ a zinc powder. It is unnecessary to apply any special activating treatment prior to the use. There is no particular restriction as to the amount of zinc to be used. However, it is usually preferred to use it in an equimolar amount to the starting material.

In the hydrogen reduction reaction, various hydrogenation catalysts may be employed, including Group VIII elements, particularly platinum group elements, rhenium, zirconium, tungsten and combinations thereof. As a support for the catalyst, alumina, activated carbon or zirconia is suitably employed. In preparing the catalyst, conventional methods for preparing noble metal catalysts can be employed. In use, it is preferred to put the catalyst preliminarily to reduction treatment to obtain stabilized properties. However, such a preliminary treatment may not necessarily be carried out.

The ratio between hydrogen and the starting material may be varied in a wide range. Usually, halogen atoms can be removed by using stoichiometric amount of hydrogen. However, in order to let the 2,2-difluoropropane starting material react completely, hydrogen may be used in an amount substantially larger than stoichiometry, for example, 4 times or more, relative to the total molar amount of the starting material.

When the reaction is carried out in the gas phase, the reaction temperature is usually from 100° to 450° C., preferably from 100° to 300° C. The contact time is usually from 0.1 to 300 seconds, preferably from 2 to 60 seconds. The reaction may be conducted in the liquid phase in the presence or absence of a solvent. As a solvent, an alcohol such as ethanol or isopropyl alcohol, acetic acid or pyridine may be employed. The reaction temperature for a liquid phase reaction is usually from room temperature to 150° C., and the reaction pressure is usually from atmospheric pressure to 10 kg/cm².

Now, the present invention will be described in further detail with reference to Examples. However, it should be understood that the present invention is by no means restricted by such specific Examples.

EXAMPLE 1-1

Into a 200 ml autoclave, 30 g (0.13 mol) of $CF_3CF_2CCl_3$, 9.1 g (0.14 mol) of zinc powder and 12 g of methanol were charged and reacted at a temperature of from 45° to 55° C. under a pressure of from 1 to 2 kg/cm² for 7 hours. Then, the reaction product was washed with dilute hydrochloric acid and then analyzed by gas chromatography. As a result, it was found that the conversion was 78%, and $CF_3CF_2CHCl_2$ formed at a selectivity of 91%.

EXAMPLE 1-2

The reaction was conducted and the product was analyzed in the same manner as in Example 1-1 except that 30 g (0.12 mol) of $CClF_2CF_2CCl_3$ was used. As a result, it was found that the conversion was 76%, and $CClF_2CF_2CHCl_2$ formed at a selectivity of 87%.

EXAMPLE 1-3

The reaction was conducted and the product was analyzed in the same manner as in Example 1-1 except that 32 g (0.12 mol) of $CCl_2FCF_2CCl_3$ was used. As a result, it was found that the conversion was 81%, and $CCl_2FCF_2CHCl_2$ formed at a selectivity of 86%.

EXAMPLE 1-4

The reaction was conducted and the product was analyzed in the same manner as in Example 1-1 except that 22 g (0.12 mol) of $CH_3CF_2CCl_3$ was used. As a result, it was found that the conversion was 77%, and $CH_3CF_2CHCl_2$ formed at a selectivity of 85%.

EXAMPLE 1-5

The reaction was conducted and the product was analyzed in the same manner as in Example 1-1 except that 24 g (0.12 mol) of $CH_2FCF_2CCl_3$ was used. As a result, it was found that the conversion was 78%, and $CH_2FCF_2CHCl_2$ formed at a selectivity of 85%.

EXAMPLE 1-6

The reaction was conducted and the product was analyzed in the same manner as in Example 1-1 except that 26 g (0.12 mol) of $CHF_2CF_2CCl_3$ was used. As a result, it was found that the conversion was 80%, and $CHF_2CF_2CHCl_2$ formed at a selectivity of 83%.

EXAMPLE 1-7

The reaction was conducted and the product was analyzed in the same manner as in Example 1-1 except that 28 g (0.12 mol) of $CHClFCF_2CCl_3$ was used. As a result, it was found that the conversion was 75%, and $CHClFCF_2CHCl_2$ formed at a selectivity of 80%.

EXAMPLE 1-8

The reaction was conducted and the product was analyzed in the same manner as in Example 1-1 except that 26 g (0.12 mol) of $CH_2ClCF_2CCl_3$ was used. As a result, it was found that the conversion was 73%, and $CH_2ClCF_2CHCl_2$ formed at a selectivity of 74%.

EXAMPLE 1-9

The reaction was conducted and the product was analyzed in the same manner as in Example 1-1 except that 30 g (0.12 mol) of $CHCl_2CF_2CCl_3$ was used. As a result, it was found that the conversion was 73%, and $CHCl_2CF_2CHCl_2$ formed at a selectivity of 77%.

EXAMPLE 1-10

The reaction was conducted and the product was analyzed in the same manner as in Example 1-1 except that 34 g (0.12 mol) of $CCl_3CF_2CCl_3$ was used. As a result, it was found that the conversion was 84%, and $CHCl_2CF_2CCl_3$ formed at a selectivity of 46% and $CHCl_2CF_2CHCl_2$ formed at a selectivity of 44%.

EXAMPLE 1-11 TO 1-15

The reaction was conducted and the product was analyzed in the same manner as in Example 1-1 except that the solvent was changed. The results are shown in the following Table.

TABLE 1-1

| Example No. | Solvent (g) | $CF_3CF_2CHCl_2$ Yield (%) |
|---|---|---|
| 11 | Methanol 13 | 77 |
| 12 | Methanol 6 | 76 |
| 13 | Water 10 | 51 |
| 14 | Methanol 10 Water 3 | 64 |
| 15 | Acetic acid 20 | 62 |

Preparation Example 1

Molded coconut shell activated carbon was immersed in a liquid prepared by adding 1% by weight of hydrochloric acid in deionized water and adjusting the pH, to impregnate the liquid sufficiently even into the interior of pores. An aqueous solution having palladium chloride dissolved in an amount of 0.5%, as a total weight of the metal component, based on the weight of the activated carbon, was gradually dropwise added thereto to let the activated carbon adsorb the ion component. An aqueous hydrazine solution was added thereto for rapid reduction. The treated activated carbon was washed with deionized water and dried at 150° C. for 5 hours.

Preparation Example 2

Pulverized coconut shell activated carbon was immersed in deionized water to impregnate water sufficiently even into the interior of pores. An aqueous solution having chloroplatinic acid dissolved in an amount of 0.5%, as the total weight of the metal component, based on the weight of the activated carbon, was gradually dropwise added thereto to let the activated carbon adsorb the ion component. The treated activated carbon was washed with deionized water and then dried at 150° C. for 5 hours. Then, it was dried in nitrogen at 550° C. for 4 hours. Then, hydrogen was introduced, and the reduction was conducted for 5 hours at 250° C.

EXAMPLE 2-1

An Inconnel 600 reaction tube having an inner diameter of 2.54 cm and a length of 100 cm packed with 400 cc of a palladium catalyst prepared in the same manner as in Preparation Example 1, was immersed in a salt bath furnace. Hydrogen and starting material 2,2-difluoropentachloropropane were gasified in a molar ratio of 3:1 and introduced into the reaction tube. The reaction temperature was 200° C., and the contact time was 20 seconds. After removal of acid components, the reaction product was collected in a trap cooled to −78° C. The collected reaction product was analyzed by gas chromatography and by NMR. The results are show in Table 2-1.

EXAMPLES 2-2 AND 2-3

The hydrogenation reaction of 2,2-difluoropentachloropropane and the analysis of the reaction product were conducted in the same manner as in Example 2-1 except that the hydrogenation catalyst as identified in Table 2-1 which was prepared in the same manner as in Preparation Example 2 except that the catalyst component was changed as shown in Table 2-1, was used and the reaction conditions as identified in Table 2-1 were employed. The results are shown in Table 2-1.

TABLE 2-1

| Example No. | 2-1 | 2-2 | 2-3 |
|---|---|---|---|
| Catalyst | Pd | Pt | Ru |
| Support | Activated carbon | Activated carbon | Activated carbon |
| Reaction temp. (°C.) | 200 | 200 | 250 |
| Ratio of $H_2$/starting material (molar ratio) | 3 | 3 | 3 |
| Contact time (sec) | 20 | 20 | 20 |
| Conversion (%) | 99.9 | 97.9 | 56.3 |
| Selectivity (%) | | | |
| $CCl_3CF_2CH_2Cl$ | 11.7 | 17.3 | 0.2 |
| $CHCl_2CF_2CHCl_2$ | 2.1 | 4.1 | 0.3 |
| $CCl_3CF_2CH_3$ | 12.7 | 28.5 | 65.1 |
| $CHCl_2CF_2CH_2Cl$ | 1.6 | 2.1 | 0.1 |
| $CHCl_2CF_2CH_3$ | 39.1 | 33.1 | 0.2 |
| $CH_2ClCF_2CH_2Cl$ | 0.7 | 0.1 | 0.1 |
| $CH_2ClCF_2CH_3$ | 24.1 | 11.3 | 0.3 |
| $CH_3CF_2CH_3$ | 2.3 | 1.7 | 11.3 |

EXAMPLES 2-4 TO 2-6

The hydrogenation reaction of 2,2-difluoropentachloropropane and the analysis of the reaction product were conducted in the same manner as in Example 2-1 except that the hydrogenation catalyst as identified in Table 2-2 which was prepared in the same manner as in Preparation Example 2 except that the catalyst component was changed as shown in Table 2-2 and the reduction temperature of the catalyst was changed to 280° C., was used and the reaction conditions as identified in Table 2-2 were employed. The results are shown in Table 2-2.

EXAMPLES 2-7 AND 2-8

The hydrogenation reaction of 2,2-difluoropentachloropropane and the analysis of the reaction product were conducted in the same manner as in Example 2-1 except that the hydrogenation catalyst as identified in Table 2-3 which was prepared in the same manner as in Preparation Example 2 except that the catalyst component was changed as shown in Table 2-3 and the reduction temperature of the catalyst was changed to 300° C., was used and the reaction conditions as identified in Table 2-3 were employed. The results are shown in Table 2-3.

TABLE 2-2

| Example No. | 2-4 | 2-5 | 2-6 |
|---|---|---|---|
| Catalyst | Rh | Pd—Ni (9:1) | Pd—Co (9:1) |
| Support | Activated carbon | Activated carbon | Activated carbon |
| Reaction temp. (°C.) | 200 | 250 | 250 |
| Ratio of $H_2$/starting material (molar ratio) | 3 | 3 | 3 |
| Contact time (sec) | 20 | 20 | 20 |
| Conversion (%) | 84.3 | 86.7 | 87.6 |
| Selectivity (%) | | | |
| $CCl_3CF_2CH_2Cl$ | 16.5 | 10.1 | 10.4 |
| $CHCl_2CF_2CHCl_2$ | 3.0 | 3.1 | 2.1 |
| $CCl_3CF_2CH_3$ | 36.8 | 12.5 | 17.0 |
| $CHCl_2CF_2CH_2Cl$ | 1.1 | 1.7 | 0.7 |
| $CHCl_2CF_2CH_3$ | 21.9 | 36.1 | 34.1 |
| $CH_2ClCF_2CH_2Cl$ | 0.1 | 0.1 | 0.7 |
| $CH_2ClCF_2CH_3$ | 14.0 | 26.3 | 32.3 |
| $CH_3CF_2CH_3$ | 4.6 | 2.1 | 1.6 |

TABLE 2-3

| Example No. | 2-7 | 2-8 |
|---|---|---|
| Catalyst | Pt—ReOx (65:35) | Pd—W (95:5) |
| Support | Activated carbon | Activated carbon |
| Reaction temp. (°C.) | 250 | 250 |
| Ratio of $H_2$/starting material (molar ratio) | 3 | 3 |
| Contact time (sec) | 20 | 20 |
| Conversion (%) | 89.7 | 93.8 |
| Selectivity (%) | | |
| $CCl_3CF_2CH_2Cl$ | 8.3 | 11.0 |
| $CHCl_2CF_2CHCl_2$ | 2.9 | 2.1 |
| $CCl_3CF_2CH_3$ | 16.1 | 12.9 |
| $CHCl_2CF_2CH_2Cl$ | 0.5 | 1.5 |
| $CHCl_2CF_2CH_3$ | 37.1 | 40.1 |
| $CH_2ClCF_2CH_2Cl$ | 0.1 | 0.7 |
| $CH_2ClCF_2CH_3$ | 31.9 | 22.3 |
| $CH_3CF_2CH_3$ | 1.3 | 2.4 |

EXAMPLES 2-9 TO 2-11

The hyrogenation reaction of 2,2-difluorohexachloropropane and the analysis of the reaction product were conducted in the same manner as in Example 2-1 except that the hydrogenation catalyst as identified in Table 2-4 which was prepared in the same manner as in Preparation Example 1 except that the catalyst component was changed as shown in Table 2-4, was used and the reaction conditions as identified in Table 2-4 were employed. The results are shown in Table 2-4.

EXAMPLES 2-12 TO 2-14

The hyrogenation reaction of 2,2-difluorohexachloropropane and the analysis of the reaction product were conducted in the same manner as in Example 2-1 except that the hydrogenation catalyst as identified in Table 2-5 which was prepared in the same manner as in Preparation Example 2 except that the catalyst component was changed as shown in Table 2-5 and the reduction temperature of the catalyst was changed to 280° C., was used and the reaction conditions as identified in Table 2-5 were employed. The results are shown in Table 2-5.

TABLE 2-4

| Example No. | 2-9 | 2-10 | 2-11 |
|---|---|---|---|
| Catalyst | Pd | Pt | Ru |
| Support | Activated carbon | Activated carbon | Activated carbon |
| Reaction temp. (°C.) | 200 | 200 | 250 |

TABLE 2-4-continued

| Example No. | 2-9 | 2-10 | 2-11 |
|---|---|---|---|
| Ratio of $H_2$/starting material (molar ratio) | 5 | 5 | 5 |
| Contact time (sec) | 20 | 20 | 20 |
| Conversion (%) | 99.9 | 99.9 | 62.1 |
| Selectivity (%) | | | |
| $CCl_3CF_2CHCl_2$ | 5.6 | 6.1 | 0.1 |
| $CHCl_2CF_2CHCl_2$ | 2.0 | 3.8 | 0.1 |
| $CCl_3CF_2CH_2Cl$ | 7.2 | 6.4 | 0.2 |
| $CHCl_2CF_2CH_2Cl$ | 8.4 | 15.8 | 0.1 |
| $CCl_3CF_2CH_3$ | 0.6 | 0.2 | 56.1 |
| $CHCl_2CF_2CH_3$ | 27.9 | 35.0 | 0.1 |
| $CH_2ClCF_2CH_2Cl$ | 8.4 | 4.0 | — |
| $CH_2ClCF_2CH_3$ | 16.8 | 15.0 | — |
| $CH_3CF_2CH_3$ | 5.6 | 3.0 | 12.1 |

TABLE 2-5

| Example No. | 2-12 | 2-13 | 2-14 |
|---|---|---|---|
| Catalyst | Rh | Pd—Ni (85:15) | Pt—Co (9:1) |
| Support | Activated carbon | Activated carbon | Activated carbon |
| Reaction temp. (°C.) | 200 | 250 | 250 |
| Ratio of $H_2$/starting material (molar ratio) | 5 | 5 | 5 |
| Contact time (sec) | 20 | 20 | 20 |
| Conversion (%) | 75.6 | 86.1 | 88.7 |
| Selectivity (%) | | | |
| $CCl_3CF_2CHCl_2$ | 5.0 | 4.0 | 3.8 |
| $CHCl_2CF_2CHCl_2$ | 4.6 | 4.8 | 5.1 |
| $CCl_3CF_2CH_2Cl$ | 9.4 | 10.8 | 11.1 |
| $CHCl_2CF_2CH_2Cl$ | 8.4 | 7.5 | 7.6 |
| $CCl_3CF_2CH_3$ | 0.7 | 0.6 | 0.7 |
| $CHCl_2CF_2CH_3$ | 35.4 | 33.9 | 34.1 |
| $CH_2ClCF_2CH_2Cl$ | 0.9 | 0.8 | 0.9 |
| $CH_2ClCF_2CH_3$ | 19.3 | 20.1 | 21.6 |
| $CH_3CF_2CH_3$ | 5.0 | 5.9 | 4.1 |

EXAMPLES 2-15 AND 2-16

The hyrogenation reaction of 2,2-difluorohexachloropropane and the analysis of the reaction product were conducted in the same manner as in Example 2-1 except that the hydrogenation catalyst as identified in Table 2-6 which was prepared in the same manner as in Preparation Example 2 except that the catalyst component was changed as shown in Table 2-6 and the reduction temperature of the catalyst was changed to 300° C., was used and the reaction conditions as identified in Table 2-6 were employed. The results are shown in Table 2-6.

TABLE 2-6

| Example No. | 2-15 | 2-16 |
|---|---|---|
| Catalyst | Pt—Re (70:30) | Pd—W (95:5) |
| Support | Activated carbon | Activated carbon |
| Reaction temp. (°C.) | 250 | 250 |
| Ratio of $H_2$/starting material (molar ratio) | 5 | 5 |
| Contact time (sec) | 20 | 20 |
| Conversion (%) | 85.7 | 95.1 |
| Selectivity (%) | | |
| $CCl_3CF_2CHCl_2$ | 5.8 | 5.1 |
| $CHCl_2CF_2CHCl_2$ | 4.1 | 4.3 |

TABLE 2-6-continued

| Example No. | 2-15 | 2-16 |
|---|---|---|
| $CCl_3CF_2CH_2Cl$ | 16.5 | 7.1 |
| $CHCl_2CF_2CH_2Cl$ | 6.1 | 8.4 |
| $CCl_3CF_2CH_3$ | 0.3 | 0.5 |
| $CHCl_2CF_2CH_3$ | 34.1 | 28.1 |
| $CH_2ClCF_2CH_2Cl$ | 3.0 | 8.5 |
| $CH_2ClCF_2CH_3$ | 16.1 | 17.1 |
| $CH_3CF_2CH_3$ | 4.1 | 5.1 |

EXAMPLE 2-17

The reaction was conducted and the reaction product was analyzed in the same manner as in Example 2-1 except that 1,1,1,3-tetrachloro-2,2-difluoropropane was used as the starting material and the reaction conditions as identified in Table 2-7 were employed. The results are shown in Table 2-7.

EXAMPLE 2-18

The reaction was conducted and the reaction product was analyzed in the same manner as in Example 2-1 except that 1,1,3,3-tetrachloro-2,2-difluoropropane was used as the starting material and the reaction conditions as identified in Table 2-7 were employed. The results are shown in Table 2-7.

EXAMPLE 2-19

The reaction was conducted and the reaction product was analyzed in the same manner as in Example 2-1 except that 1,1,1-trichloro-2,2-difluoropropane was used as the starting material and the reaction conditions as identified in Table 2-7 were employed. The results are shown in Table 2-7.

TABLE 2-7

| Example No. | 2-17 | 2-18 | 2-19 |
|---|---|---|---|
| Catalyst | Pd | Pd | Pd |
| Support | Activated carbon | Activated carbon | Activated carbon |
| Reaction temp. (°C.) | 200 | 200 | 200 |
| Ratio of $H_2$/starting material (molar ratio) | 3 | 3 | 2 |
| Contact time (sec) | 20 | 20 | 20 |
| Conversion (%) | 90.9 | 91.2 | 92.7 |
| Selectivity (%) | | | |
| $CCl_3CF_2CH_3$ | 10.1 | | |
| $CHCl_2CF_2CH_2Cl$ | 2.3 | 16.1 | |
| $CHCl_2CF_2CH_3$ | 16.8 | 39.6 | 52.1 |
| $CH_2ClCF_2CH_2Cl$ | 0.9 | 3.8 | |
| $CH_2ClCF_2CH_3$ | 39.6 | 18.8 | 13.5 |
| $CH_3CF_2CH_3$ | 29.3 | 16.4 | 32.9 |

EXAMPLE 2-20

The reaction was conducted and the reaction product was analyzed in the same manner as in Example 2-1 except that 1,1,3-trichloro-2,2-difluoropropane was used as the starting material and the reaction conditions as identified in Table 2-8 were employed. The results are shown in Table 2-8.

EXAMPLE 2-21

The reaction was conducted and the reaction product was analyzed in the same manner as in Example 2-1 except that 1,1-dichloro-2,2-difluoropropane was used as the starting material and the reaction conditions as identified in Table 2-8 were employed. The results are shown in Table 2-8.

TABLE 2-8

| Example No. | 2-20 | 2-21 |
|---|---|---|
| Catalyst | Pd | Pd |
| Support | Activated carbon | Activated carbon |
| Reaction temp. (°C.) | 200 | 200 |
| Ratio of $H_2$/starting material (molar ratio) | 2 | 2 |
| Contact time (sec) | 20 | 20 |
| Conversion (%) | 89.4 | 76.0 |
| Selectivity (%) | | |
| $CHCl_2CF_2CH_3$ | 29.4 | |
| $CH_2ClCF_2CH_2Cl$ | 21.6 | |
| $CH_2ClCF_2CH_3$ | 33.6 | 45.3 |
| $CH_3CF_2CH_3$ | 15.4 | 53.0 |

EXAMPLE 2-22

The reaction was conducted and the reaction product was analyzed in the same manner as in Example 2-1 except that 1,3-dichloro-2,2-difluoropropane was used as the starting material and the reaction conditions as identified in Table 2-9 were employed. The results are shown in Table 2-9.

EXAMPLE 2-23

The reaction was conducted and the reaction product was analyzed in the same manner as in Example 2-1 except that 1-chloro-2,2-difluoropropane was used as the starting material and the reaction conditions as identified in Table 2-9 were employed. The results are shown in Table 2-9.

TABLE 2-9

| Example No. | 2-22 | 2-23 |
|---|---|---|
| Catalyst | Pd | Pd |
| Support | Activated carbon | Activated carbon |
| Reaction temp. (°C.) | 200 | 200 |
| Ratio of $H_2$/starting material (molar ratio) | 2 | 1 |
| Contact time (sec) | 20 | 20 |
| Conversion (%) | 79.6 | 66.1 |
| Selectivity (%) | | |
| $CH_2ClCF_2CH_3$ | 42.1 | |
| $CH_3CF_2CH_3$ | 55.9 | 87.0 |

EXAMPLE 2-24

The reaction was conducted and the reaction product was analyzed in the same manner as in Example 2-1 except that a platinum catalyst prepared in the same manner as in Preparation Example 2 was used as the hydrogenation catalyst and 1,1,1,3-tetrachloro-2,2-difluoropropane was used as the starting material, and the reaction conditions as identified in Table 2-10 were employed. The results are shown in Table 2-10.

EXAMPLE 2-25

The reaction was conducted and the reaction product was analyzed in the same manner as in Example 2-1 except that a platinum catalyst prepared in the same manner as in Preparation Example 2 was used as the hydrogenation catalyst and 1,1,3,3-tetrachloro-2,2-difluoropropane was used as the starting material, and the reaction conditions as identified in Table 2-10 were employed. The results are shown in Table 2-10.

EXAMPLE 2-26

The reaction was conducted and the reaction product was analyzed in the same manner as in Example 2-1 except that a platinum catalyst prepared in the same manner as in Preparation Example 2 was used as the hydrogenation catalyst and 1,1,1-trichloro-2,2-difluoropropane was used as the starting material, and the reaction conditions as identified in Table 2-10 were employed. The results are shown in Table 2-10.

TABLE 2-10

| Example No. | 2-24 | 2-25 | 2-26 |
|---|---|---|---|
| Catalyst | Pt | Pt | Pt |
| Support | Activated carbon | Activated carbon | Activated carbon |
| Reaction temp. (°C.) | 200 | 200 | 200 |
| Ratio of $H_2$/starting material (molar ratio) | 3 | 3 | 2 |
| Contact time (sec) | 20 | 20 | 20 |
| Conversion (%) | 90.1 | 93.1 | 93.4 |
| Selectivity (%) | | | |
| $CCl_3CF_2CH_3$ | 13.1 | | |
| $CHCl_2CF_2CH_2Cl$ | 4.1 | 18.1 | |
| $CHCl_2CF_2CH_3$ | 19.1 | 40.3 | 65.4 |
| $CH_2ClCF_2CH_2Cl$ | 0.7 | 5.1 | |
| $CH_2ClCF_2CH_3$ | 37.8 | 21.5 | 20.1 |
| $CH_3CF_2CH_3$ | 25.2 | 13.7 | 13.9 |

EXAMPLE 2-27

The reaction was conducted and the reaction product was analyzed in the same manner as in Example 2-1 except that a platinum catalyst prepared in the same manner as in Preparation Example 2 was used as the hydrogenation catalyst and 1,1,3-trichloro-2,2-difluoropropane was used as the starting material, and the reaction conditions as identified in Table 2-11 were employed. The results are shown in Table 2-11.

EXAMPLE 2-28

The reaction was conducted and the reaction product was analyzed in the same manner as in Example 2-1 except that a platinum catalyst prepared in the same manner as in Preparation Example 2 was used as the hydrogenation catalyst and 1,1-dichloro-2,2-difluoropropane was used as the starting material, and the reaction conditions as identified in Table 2-11 were employed. The results are shown in Table 2-11.

TABLE 2-11

| Example No. | 2-27 | 2-28 |
|---|---|---|
| Catalyst | Pt | Pt |
| Support | Activated carbon | Activated carbon |
| Reaction temp. (°C.) | 200 | 200 |
| Ratio of $H_2$/starting material (molar ratio) | 2 | 2 |
| Contact time (sec) | 20 | 20 |
| Conversion (%) | 87.6 | 72.9 |
| Selectivity (%) | | |
| $CHCl_2CF_2CH_3$ | 31.6 | |

TABLE 2-11-continued

| Example No. | 2-27 | 2-28 |
|---|---|---|
| $CH_2ClCF_2CH_2Cl$ | 26.3 | |
| $CH_2ClCF_2CH_3$ | 34.6 | 63.0 |
| $CH_3CF_2CH_3$ | 7.5 | 36.2 |

EXAMPLE 2-29

The reaction was conducted and the reaction product was analyzed in the same manner as in Example 2-1 except that a platinum catalyst prepared in the same manner as in Preparation Example 2 was used as the hydrogenation catalyst and 1,3-dichloro-2,2-difluoropropane was used as the starting material, and the reaction conditions as identified in Table 2-12 were employed. The results are shown in Table 2-12.

EXAMPLE 2-30

The reaction was conducted and the reaction product was analyzed in the same manner as in Example 2-1 except that a platinum catalyst prepared in the same manner as in Preparation Example 2 was used as the hydrogenation catalyst and 1-chloro-2,2-difluoropropane was used as the starting material, and the reaction conditions as identified in Table 2-12 were employed. The results are shown in Table 2-12.

TABLE 2-12

| Example No. | 2-29 | 2-30 |
|---|---|---|
| Catalyst | Pt | Pt |
| Support | Activated carbon | Activated carbon |
| Reaction temp. (°C.) | 200 | 200 |
| Ratio of $H_2$/starting material (molar ratio) | 2 | 1 |
| Contact time (sec) | 20 | 20 |
| Conversion (%) | 77.0 | 65.4 |
| Selectivity (%) | | |
| $CH_2ClCF_2CH_3$ | 43.9 | 63.0 |
| $CH_3CF_2CH_3$ | 52.8 | 36.2 |

EXAMPLE 2-31

Into a 1 SUS316 autoclave, 750 g of 2,2-difluoropentachloropropane and 7.5 g of a platinum catalyst prepared in the same manner as in Preparation Example 2 except that activated carbon powder was used as a support and the amount of the supported catalyst was changed to 5% by weight, as a reduction catalyst, were charged. Further, a condenser was attached to an upper portion of the flange of the autoclave and a valve was attached to an upper portion of the condenser to control the reaction pressure. The temperature of the cooling medium of the condenser was −20° C.

The inside of the autoclave was thoroughly replaced by nitrogen, and then the temperature was raised to 65° C. under stirring. Then, hydrogen was blown thereinto until the inner pressure became 2 kg/cm². Thereafter, hydrogen was introduced at a constant flow rate so that the inner pressure was maintained at a level of 2 kg/cm², and the temperature was maintained at a level of about 60° C. The flow rate of the hydrogen at that time was 56 ml/min. The reaction gas which was not condensed by the condenser was passed through water to remove hydrogen chloride and then passed through a trap cooled by dry ice, and the condensed product was collected.

Under such a state, the reaction was conducted for 120 hours under stirring. Then, the reaction solution was collected, and the catalyst was recovered by filtration. A mixture of the filtrate and the condensed product cooled in the trap cooled by dry ice, was analyzed by gas chromatography. The results are shown in Table 2-13.

TABLE 2-13

| Conversion (%) | 66.3 |
|---|---|
| Selectivity (%) | |
| $CCl_3CF_2CH_2Cl$ | 17.3 |
| $CHCl_2CF_2CHCl_2$ | 2.1 |
| $CCl_3CF_2CH_3$ | 27.5 |
| $CHCl_2CF_2CH_2Cl$ | 1.6 |
| $CHCl_2CF_2CH_3$ | 36.1 |
| $CH_2ClCF_2CH_2Cl$ | 2.4 |
| $CH_2ClCF_2CH_3$ | 7.1 |
| $CH_3CF_2CH_3$ | 2.3 |

EXAMPLE 3-1

An Inconnel 600 reaction tube having an inner diameter of 2.54 cm and a length of 100 cm packed with 400 cc of a reduction catalyst prepared in the same manner as in Preparation Example 1 except that the reducing agent was changed to sodium borohydride, was immersed in a salt bath furnace.

Hydrogen and starting material 1,1-dichlorohexafluoropropane were gasified in a molar ratio of 2:1 and introduced into the reaction tube. The reaction temperature was 200° C., and the contact time was seconds. After removing acid components, the reaction product was collected in a trap cooled to −78° C. The collected reaction product was analyzed by gas chromatography and by NMR. The results are shown in Table 3-1.

EXAMPLE 3-2

The hydrogenation reaction of 1,1-dichlorohexafluoropropane was conducted and the reaction product was analyzed in the same manner as in Example 3-1 except that the hydrogenation catalyst prepared in the same manner as in Preparation Example 2 except that the amount of the supported catalyst was changed to 2% by weight, was used and the reaction conditions as identified in Table 3-1 were employed. The results are shown in Table 3-1.

TABLE 3-1

| Example No. | 3-1 | 3-2 |
|---|---|---|
| Catalyst | Pd | Pt |
| Support | Activated carbon | Activated carbon |
| Reaction temp. (°C.) | 200 | 200 |
| Ratio of $H_2$/starting material (molar ratio) | 2 | 2 |
| Contact time (sec) | 20 | 20 |
| Conversion (%) | 94.2 | 90.8 |
| Selectivity (%) | | |
| $CF_3CF_2CHClF$ | 52.0 | 57.1 |
| $CF_3CF_2CH_2F$ | 43.6 | 40.9 |
| $CF_3CF_2CH_3$ | 4.1 | 1.8 |

EXAMPLES 3-3 AND 3-4

The hydrogenation reaction of 1,1-dichlorohexafluoropropane was conducted and the reaction product was analyzed in the same manner as in Example 3-1 except that the hydrogenation catalyst as identified in Table 3-2 which was prepared in the same manner as in Preparation Example 1 except that the catalyst component was changed as shown in Table 3-2, the amount of the supported catalyst was changed to 5% by weight and the reducing agent was changed to potassium borohydride, was used and the reaction conditions as identified in Table 3-2 were employed. The results are shown in Table 3-2.

TABLE 3-2

| Example No. | 3-3 | 3-4 |
| --- | --- | --- |
| Catalyst | Ru | Rh |
| Support | Activated carbon | Activated carbon |
| Reaction temp. (°C.) | 250 | 200 |
| Ratio of $H_2$/starting material (molar ratio) | 2 | 2 |
| Contact time (sec) | 20 | 20 |
| Conversion (%) | 45.8 | 79.6 |
| Selectivity (%) | | |
| $CF_3CF_2CHClF$ | 2.3 | 44.0 |
| $CF_3CF_2CH_2F$ | 3.5 | 40.1 |
| $CF_3CF_2CH_3$ | 75.9 | 15.6 |

EXAMPLES 3-5 AND 3-6

The hydrogenation reaction of 1,1-dichlorohexafluoropropane was conducted and the reaction product was analyzed in the same manner as in Example 3-1 except that the reaction conditions as identified in Table 3-3 were employed and the hydrogenation catalyst as identified in Table 3-3 which was prepared in the same manner as in Preparation Example 2 except that the catalyst component was changed as shown in Table 3-3, the amount of the supported catalyst was changed to 2% by weight and the conditions for the reduction of the catalyst was changed to 290° C. for 5 hours, was used. The results are shown in Table 3-3.

TABLE 3-3

| Example No. | 3-5 | 3-6 |
| --- | --- | --- |
| Catalyst | Pd—Ni (9:1) | Pd—Co (9:1) |
| Support | Activated carbon | Activated carbon |
| Reaction temp. (°C.) | 250 | 250 |
| Ratio of $H_2$/starting material (molar ratio) | 2 | 2 |
| Contact time (sec) | 20 | 20 |
| Conversion (%) | 77.1 | 78.9 |
| Selectivity (%) | | |
| $CF_3CF_2CHClF$ | 41.5 | 39.6 |
| $CF_3CF_2CH_2F$ | 43.0 | 41.8 |
| $CF_3CF_2CH_3$ | 15.0 | 18.4 |

EXAMPLES 3-7 AND 3-8

The hydrogenation reaction of 1,1-dichlorohexafluoropropane was conducted and the reaction product was analyzed in the same manner as in Example 3-1 except that the reaction conditions as identified in Table 3-4 were employed and the hydrogenation catalyst as identified in Table 3-4 which was prepared in the same manner as in Preparation Example 2 except that the catalyst component was changed as shown in Table 3-4, the amount of the supported catalyst was changed to 5% by weight, the support was changed to molded coconut shell activated carbon and the conditions for the reduction of the catalyst was changed to 300° C. for 5 hours, was used. The results are shown in Table 3-4.

TABLE 3-4

| Example No. | 3-7 | 3-8 |
| --- | --- | --- |
| Catalyst | Pt—ReOx (6:4) | Pd—W (9:1) |
| Support | Activated carbon | Activated carbon |
| Reaction temp. (°C.) | 250 | 250 |
| Ratio of $H_2$/starting material (molar ratio) | 2 | 2 |
| Contact time (sec) | 20 | 20 |
| Conversion (%) | 74.9 | 83.6 |
| Selectivity (%) | | |
| $CF_3CF_2CHClF$ | 48.1 | 53.7 |
| $CF_3CF_2CH_2F$ | 39.5 | 41.6 |
| $CF_3CF_2CH_3$ | 11.8 | 4.6 |

EXAMPLE 3-9

The reaction was conducted and the reaction product was analyzed in the same manner as in Example 3-1 except that 1,3-dichlorohexafluoropropane was used as the starting material and the reaction conditions as identified in Table 3-5 were employed. The results are shown in Table 3-5.

EXAMPLE 3-10

The reaction was conducted and the reaction product was analyzed in the same manner as in Example 3-1 except that 1-chloro-1,1,2,2,3,3-hexafluoropropane was used as the starting material and the reaction conditions as identified in Table 3-5 were employed. The results are shown in Table 3-5.

EXAMPLE 3-11

The reaction was conducted and the reaction product was analyzed in the same manner as in Example 3-1 except that 1-chloro-1,2,2,3,3,3-hexafluoropropane was used as the starting material and the reaction conditions as identified in Table 3-5 were employed. The results are shown in Table 3-5.

TABLE 3-5

| Example No. | 3-9 | 3-10 | 3-11 |
| --- | --- | --- | --- |
| Catalyst | Pd | Pd | Pd |
| Reaction temp. (°C.) | 250 | 250 | 200 |
| Ratio of $H_2$/starting material (molar ratio) | 3 | 3 | 3 |
| Contact time (sec) | 30 | 30 | 30 |
| Conversion (%) | 51.3 | 79.3 | 97.8 |
| Selectivity (%) | | | |
| $CClF_2CF_2CHF_2$ | 68.3 | | |
| $CHF_2CF_2CHF_2$ | 31.4 | 92.8 | |
| $CF_3CF_2CH_2F$ | | | 82.9 |
| $CF_3CF_2CH_3$ | | | 15.7 |

EXAMPLE 3-12

The reaction was conducted and the reaction product was analyzed in the same manner as in Example 3-1 except that a platinum catalyst prepared in the same manner as in Preparation Example 1 except that pulverized coconut shell activated carbon was used as the support, the amount of supported catalyst was 1% by weight and the reducing agent was changed to potassium borohydride, was used, 1,3-dichlorohexafluoropropane was used as the starting material and the reaction conditions as identified in Table 3-6 were employed. The results are shown in Table 3-6.

EXAMPLE 3-13

The reaction was conducted and the reaction product was analyzed in the same manner as in Example 3-1 except that as the hydrogenation catalyst, a platinum catalyst prepared in the same manner as in Preparation Example 2 was used, 1-chloro-1,1,2,2,3,3-hexafluoropropane was used as the starting material and the reaction conditions as shown in Table 3-6 were employed. The results are shown in Table 3-6.

EXAMPLE 3-14

The reaction was conducted and the reaction product was analyzed in the same manner as in Example 3-1 except that as the hydrogenation catalyst, a platinum catalyst prepared in the same manner as in Preparation Example 2 except that the support was a molded coconut shell activated carbon and the amount of the supported catalyst was 5% by weight, was used, 1-chloro-1,2,2,3,3,3-hexafluoropropane was used as the starting material and the reaction conditions as identified in Table 3-6 were employed. The results are shown in Table 3-6.

TABLE 3-6

| Example No. | 3-12 | 3-13 | 3-14 |
|---|---|---|---|
| Catalyst | Pt | Pt | Pt |
| Support | Activated carbon | Activated carbon | Activated carbon |
| Reaction temp. (°C.) | 250 | 250 | 200 |
| Ratio of $H_2$/starting material (molar ratio) | 3 | 3 | 3 |
| Contact time (sec) | 30 | 30 | 20 |
| Conversion (%) | 46.1 | 75.4 | 98.0 |
| Selectivity (%) | | | |
| $CClF_2CF_2CHF_2$ | 77.6 | | |
| $CHF_2CF_2CHF_2$ | 22.0 | 95.4 | |
| $CF_3CF_2CH_2F$ | | | 80.7 |
| $CF_3CF_2CH_3$ | | | 17.8 |

EXAMPLE 3-15

Into a 1 SUS316 autoclave, 750 g of 1,1-dichlorohexafluoropropane and 7.5 g of a catalyst prepared in the same manner as in Preparation Example 1 except that the catalyst component was platinum, the carrier was activated carbon powder, the amount of the supported catalyst was 5% by weight and the reducing agent was sodium borohydride, were charged. A condenser was attached at the upper portion of the flange of the autoclave, and a valve was attached at the upper portion of the condenser to control the reaction pressure. The temperature of the cooling medium for the condenser was −20° C.

The inside of the autoclave was thoroughly replaced by nitrogen, and then the temperature was raised to 65° C. under stirring. Then, hydrogen was blown thereinto until the inner pressure became 2 kg/cm$^2$. Thereafter, hydrogen was introduced at a constant flow rate so that the inner pressure was maintained at a level of 2 kg/cm$^2$, and the temperature was maintained at about 60° C. The flow rate of the hydrogen at that time was 56 ml/min. The reaction gas which was not condensed by the condenser, was passed through water to remove hydrogen chloride and then passed through a trap cooled by dry ice, whereby the condensed product was collected.

Under such a state, the reaction was conducted for 120 hours under stirring. Then, the reaction solution was withdrawn, and the catalyst was separated by filtration. A mixture of the filtrate and the condensed product collected in the trap cooled by dry ice, was analyzed by gas chromatography. The results are shown in Table 3-7.

TABLE 3-7

| Conversion (%) | 66.3 |
|---|---|
| Selectivity (%) | |
| $CCl_3CF_2CH_2Cl$ | 17.3 |
| $CHCl_2CF_2CHCl_2$ | 2.1 |
| $CCl_3CF_2CH_3$ | 27.5 |
| $CHCl_2CF_2CH_2Cl$ | 1.6 |
| $CHCl_2CF_2CH_3$ | 36.1 |
| $CH_2ClCF_2CH_2Cl$ | 2.4 |
| $CH_2ClCF_2CH_3$ | 7.1 |
| $CH_3CF_2CH_3$ | 2.3 |

EXAMPLE 4-1

An Inconnel 600 reaction tube having an inner diameter of 2.54 cm and a length of 100 cm packed with 400 cc of a palladium catalyst supported on activated carbon (amount of supported catalyst: 0.5% by weight), was immersed in a salt bath furnace.

Hydrogen and starting material 1,1,1-trichloro-2,2,3,3,3-pentafluoropropane were gasified in a molar ratio of 1:1 and introduced into the reaction tube. The reaction temperature was 200° C., and the contact time was seconds. After removing acid components, the reaction product was collected in a trap cooled to −78° C. The collected reaction product was analyzed by gas chromatography and by NMR. The results are shown in Table 4-1.

EXAMPLES 4-2 AND 4-3

The hydrogenation reaction of 1,1,1-trichloro-2,2,3,3,3-pentafluoropropane was conducted and the reaction product was analyzed in the same manner as in Example 4-1 except that the hydrogenation catalyst as identified in Table 4-1 which was prepared in the same manner as in Preparation Example 2 except that the catalyst component was changed as shown in Table 4-1, was used and the reaction conditions as identified in Table 4-1 were employed. The results are shown in Table 4-1.

TABLE 4-1

| Example No. | 4-1 | 4-2 | 4-3 |
|---|---|---|---|
| Catalyst | Pd | Pd | Pt |
| Support | Activated carbon | Activated carbon | Activated carbon |
| Reaction temp. (°C.) | 200 | 200 | 200 |
| Ratio of $H_2$/starting material (molar ratio) | 1 | 2 | 1 |
| Contact time (sec) | 20 | 20 | 20 |
| Conversion (%) | 71.9 | 99.9 | 73.9 |
| Selectivity (%) | | | |
| $CF_3CF_2CHCl_2$ | 75.3 | 23.9 | 7.8 |

TABLE 4-1-continued

| Example No. | 4-1 | 4-2 | 4-3 |
|---|---|---|---|
| $CF_3CF_2CH_2Cl$ | 11.4 | 38.5 | 13.1 |
| $CF_3CF_2CH_3$ | 13.1 | 37.6 | 6.9 |
| $CHF_2CF_2CH_3$ | | 0.1 | |

EXAMPLES 4-4 TO 4-6

The hydrogenation reaction of 1,1,1-trichloro-2,2,3,3,3-pentafluoropropane was conducted and the reaction product was analyzed in the same manner as in Example 4-1 except that the hydrogenation catalyst as identified in Table 4-2 which was prepared in the same manner as in Preparation Example 2 except that the catalyst component was changed as shown in Table 4-2, was used and the reaction conditions as identified in Table 4-2 were employed. The results are shown in Table 4-2.

TABLE 4-2

| Example No. | 4-4 | 4-5 | 4-6 |
|---|---|---|---|
| Catalyst | Pt | Ru | Rh |
| Support | Activated carbon | Activated carbon | Activated carbon |
| Reaction temp. (°C.) | 200 | 250 | 200 |
| Ratio of $H_2$/starting material (molar ratio) | 2 | 2 | 2 |
| Contact time (sec). | 20 | 20 | 20 |
| Conversion (%) | 99.9 | 55.0 | 78.1 |
| Selectivity (%) | | | |
| $CF_3CF_2CHCl_2$ | 35.1 | 8.9 | 30.7 |
| $CF_3CF_2CH_2Cl$ | 38.6 | 10.1 | 24.3 |
| $CF_3CF_2CH_3$ | 26.3 | 80.7 | 44.7 |
| $CHF_2CF_2CH_3$ | 0.1 | | |

EXAMPLES 4-7 AND 4-8

The hydrogenation reaction of 1,1,1-trichloro-2,2,3,3,3-pentafluoropropane was conducted and the reaction product was analyzed in the same manner as in Example 4-1 except that the hydrogenation catalyst as identified in Table 4-3 which was prepared in the same manner as in Preparation Example 2 except that the weight ratio of the catalyst component was changed as shown in Table 4-3, the temperature for the reduction of the catalyst was changed to 300° C., was used and the conditions for reduction as identified in Table 4-3 were employed. The results are shown in Table 4-3.

EXAMPLES 4-9 AND 4-10

The hydrogenation reaction of 1,1,1-trichloro-2,2,3,3,3-pentafluoropropane was conducted and the reaction product was analyzed in the same manner as in Example 4-1 except that the hydrogenation catalyst as identified in Table 4-3 which was prepared in the same manner as in Preparation Example 2 except that the weight ratio of the catalyst component was changed as shown in Table 4-4, the temperature for the reduction of the catalyst was changed to 300° C., was used and the conditions for reduction as identified in Table 4-4 were employed. The results are shown in Table 4-4.

TABLE 4-3

| Example No. | 4-7 | 4-8 |
|---|---|---|
| Catalyst | Pd—Ni (8:2) | Pd—Co (9:1) |
| Support | Activated carbon | Activated carbon |
| Reaction temp. (°C.) | 250 | 250 |
| Ratio of $H_2$/starting material (molar ratio) | 2 | 2 |
| Contact time (sec) | 20 | 20 |
| Conversion (%) | 68.5 | 69.0 |
| Selectivity (%) | | |
| $CF_3CF_2CHCl_2$ | 20.7 | 25.1 |
| $CF_3CF_2CH_2Cl$ | 35.0 | 35.1 |
| $CF_3CF_2CH_3$ | 44.3 | 39.6 |

TABLE 4-4

| Example No. | 4-9 | 4-10 |
|---|---|---|
| Catalyst | Pt—ReOx (1:1) | Pd—W (9:1) |
| Support | Activated carbon | Activated carbon |
| Reaction temp. (°C.) | 250 | 250 |
| Ratio of $H_2$/starting material (molar ratio) | 2 | 2 |
| Contact time (sec) | 20 | 20 |
| Conversion (%) | 70.8 | 75.9 |
| Selectivity (%) | | |
| $CF_3CF_2CHCl_2$ | 24.5 | 25.4 |
| $CF_3CF_2CH_2Cl$ | 33.6 | 36.1 |
| $CF_3CF_2CH_3$ | 41.6 | 38.1 |
| $CHF_2CF_2CH_3$ | | 0.1 |

EXAMPLES 4-11 TO 4-13

The hydrogenation reaction of 1,1,3-trichloro-1,2,2,3,3-pentafluoropropane was conducted and the reaction product was analyzed in the same manner as in Example 4-1 except that the hydrogenation catalyst as identified in Table 4-5 which was prepared in the same manner as in preparation Example 1 except that the catalyst component was changed as shown in Table 4-5, the amount of the supported catalyst was changed to 2.0% by weight, was used and the conditions for reduction as identified in Table 4-5 were employed. The results are shown in Table 4-5.

EXAMPLES 4-14 TO 4-16

The hydrogenation reaction of 1,1,3-trichloro-1,2,2,3,3-pentafluoropropane was conducted and the reaction product was analyzed in the same manner as in Example 4-1 except that the hydrogenation catalyst as identified in Table 4-6 which was prepared in the same manner as in Preparation Example 2 except that the catalyst component was changed as shown in Table 4-6, the amount of the supported catalyst was changed to 2.0% by weight, was used and the conditions for reduction as identified in Table 4-6 were employed. The results are shown in Table 4-6.

TABLE 4-5

| Example No. | 4-11 | 4-12 | 4-13 |
|---|---|---|---|
| Catalyst | Pd | Pd | Pt |
| Support | Activated carbon | Activated carbon | Activated carbon |

TABLE 4-5-continued

| Example No. | 4-11 | 4-12 | 4-13 |
|---|---|---|---|
| Reaction temp. (°C.) | 200 | 200 | 200 |
| Ratio of $H_2$/starting material (molar ratio) | 1 | 2 | 1 |
| Contact time (sec). | 20 | 20 | 20 |
| Conversion (%) | 55.7 | 99.9 | 75.0 |
| Selectivity (%) | | | |
| $CClF_2CF_2CHClF$ | 35.0 | 29.6 | 72.6 |
| $CHF_2CF_2CCl_2F$ | 0.1 | 0.1 | |
| $CClF_2CF_2CH_2F$ | 60.8 | 62.3 | 26.9 |
| $CHF_2CF_2CHClF$ | 0.1 | 0.1 | |
| $CHF_2CF_2CH_2F$ | | 0.1 | |
| $CHF_2CF_2CH_3$ | 3.7 | 7.5 | 0.4 |

TABLE 4-6

| Example No. | 4-14 | 4-15 | 4-16 |
|---|---|---|---|
| Catalyst | Pt | Ru | Rh |
| Support | Activated carbon | Activated carbon | Activated carbon |
| Reaction temp. (°C.) | 200 | 270 | 250 |
| Ratio of $H_2$/starting material (molar ratio) | 2 | 2 | 2 |
| Contact time (sec). | 20 | 20 | 20 |
| Conversion (%) | 99.9 | 50.1 | 72.0 |
| Selectivity (%) | | | |
| $CClF_2CF_2CHClF$ | 61.3 | 7.6 | 30.8 |
| $CHF_2CF_2CCl_2F$ | 0.1 | | |
| $CClF_2CF_2CH_2F$ | 37.6 | 15.8 | 25.9 |
| $CHF_2CF_2CHClF$ | 0.1 | | |
| $CHF_2CF_2CH_2F$ | 0.1 | | |
| $CHF_2CF_2CH_3$ | 0.7 | 75.9 | 43.0 |

EXAMPLES 4-17 AND 4-18

The hydrogenation reaction of 1,1,3-trichloro-1,2,2,3,3-pentafluoropropane was conducted and the reaction product was analyzed in the same manner as in Example 4-1 except that the hydrogenation catalyst prepared in the same manner as in Preparation Example 2 except that the weight ratio of the catalyst components was changed as shown in Table 4-7, the temperature for the reduction of the catalyst was changed to 300° C., was used and the conditions for reduction as identified in Table 4-7 were employed. The results are shown in Table 4-7.

EXAMPLES 4-19 AND 4-20

The hydrogenation reaction of 1,1,3-trichloro-1,2,2,3,3-pentafluoropropane was conducted and the reaction product was analyzed in the same manner as in Example 4-1 except that the hydrogenation catalyst prepared in the same manner as in Preparation Example 2 except that the weight ratio of the catalyst components was changed as shown in Table 4-8, the temperature for the reduction of the catalyst was changed to 300° C., was used and the conditions for reduction as identified in Table 4-8 were employed. The results are shown in Table 4-8.

TABLE 4-7

| Example No. | 4-17 | 4-18 |
|---|---|---|
| Catalyst | Pd—Ni (8:2) | Pd—Co (9:1) |
| Support | Activated carbon | Activated carbon |
| Reaction temp. (°C.) | 260 | 270 |
| Ratio of $H_2$/starting material (molar ratio) | 2 | 2 |
| Contact time (sec) | 20 | 20 |
| Conversion (%) | 75.3 | 68.0 |
| Selectivity (%) | | |
| $CClF_2CF_2CHClF$ | 25.3 | 28.1 |
| $CHF_2CF_2CCl_2F$ | 0.1 | 0.1 |
| $CClF_2CF_2CH_2F$ | 49.6 | 53.7 |
| $CHF_2CF_2CHClF$ | 0.1 | 0.1 |
| $CHF_2CF_2CH_2F$ | 0.1 | 0.1 |
| $CHF_2CF_2CH_3$ | 24.9 | 17.9 |

TABLE 4-8

| Example No. | 4-19 | 4-20 |
|---|---|---|
| Catalyst | Pt—ReOx (1:1) | Pd—W (9:1) |
| Support | Activated carbon | Activated carbon |
| Reaction temp. (°C.) | 260 | 260 |
| Ratio of $H_2$/starting material (molar ratio) | 2 | 2 |
| Contact time (sec) | 20 | 20 |
| Conversion (%) | 71.4 | 80.6 |
| Selectivity (%) | | |
| $CClF_2CF_2CHClF$ | 34.2 | 27.1 |
| $CHF_2CF_2CCl_2F$ | 0.1 | 0.1 |
| $CClF_2CF_2CH_2F$ | 50.9 | 55.1 |
| $CHF_2CF_2CHClF$ | 0.1 | 0.1 |
| $CHF_2CF_2CH_2F$ | 0.1 | 0.1 |
| $CHF_2CF_2CH_3$ | 14.5 | 16.8 |

EXAMPLE 4-21

The reaction was conducted and the reaction product was analyzed in the same manner as in Example 4-1 except that 1,1,dichloro-2,2,3,3,3-pentafluoropropane was used as the starting material and the reaction conditions as identified in Table 4-9 were employed. The results are shown in Table 4-9.

EXAMPLE 4-22

The reaction was conducted and the reaction product was analyzed in the same manner as in Example 4-1 except that 1,3-dichloro-1,1,2,2,3-pentafluoropropane was used as the starting material and the reaction conditions as identified in Table 4-9 were employed. The results are shown in Table 4-9.

EXAMPLE 4-23

The reaction was conducted and the reaction product was analyzed in the same manner as in Example 4-1 except that 1,1-dichloro-1,2,2,3,3-pentafluoropropane was used as the starting material and the reaction conditions as identified in Table 4-9 were employed. The results are shown in Table 4-9.

TABLE 4-9

| Example No. | 4-21 | 4-22 | 4-23 |
|---|---|---|---|
| Catalyst | Pd | Pd | Pd |

TABLE 4-9-continued

| Example No. | 4-21 | 4-22 | 4-23 |
|---|---|---|---|
| Support | Activated carbon | Activated carbon | Activated carbon |
| Reaction temp. (°C.) | 200 | 200 | 200 |
| Ratio of $H_2$/starting material (molar ratio) | 2 | 2 | 2 |
| Contact time (sec). | 20 | 20 | 20 |
| Conversion (%) | 99.9 | 99.9 | 99.9 |
| Selectivity (%) | | | |
| $CF_3CF_2CH_2Cl$ | 38.7 | | |
| $CF_3CF_2CH_3$ | 60.5 | | |
| $CClF_2CF_2CH_2F$ | | 35.1 | |
| $CHF_2CF_2CHClF$ | | 0.1 | 8.9 |
| $CHF_2CF_2CH_2F$ | | 0.2 | 69.5 |
| $CClF_2CF_2CH_3$ | | 55.9 | |
| $CHF_2CF_2CH_3$ | 0.3 | 5.5 | 20.4 |

EXAMPLE 4-24

The reaction was conducted and the reaction product was analyzed in the same manner as in Example 4-1 except that 1-chloro-2,2,3,3,3-pentafluoropropane was used as the starting material and the reaction conditions as identified in Table 4-10 were employed. The results are shown in Table 4-10.

EXAMPLE 4-25

The reaction was conducted and the reaction product was analyzed in the same manner as in Example 4-1 except that 1-chloro-1,1,2,2,3-pentafluoropropane was used as the starting material and the reaction conditions as identified in Table 4-10 were employed. The results are shown in Table 4-10.

EXAMPLE 4-26

The reaction was conducted and the reaction product was analyzed in the same manner as in Example 4-1 except that 1-chloro-1,2,2,3,3-pentafluoropropane was used as the starting material and the reaction conditions as identified in Table 4-10 were employed. The results are shown in Table 4-10.

TABLE 4-10

| Example No. | 4-24 | 4-25 | 4-26 |
|---|---|---|---|
| Catalyst | Pd | Pd | Pd |
| Support | Activated carbon | Activated carbon | Activated carbon |
| Reaction temp. (°C.) | 200 | 250 | 200 |
| Ratio of $H_2$/starting material (molar ratio) | 2 | 2 | 2 |
| Contact time (sec). | 20 | 30 | 20 |
| Conversion (%) | 99.9 | 95.8 | 99.9 |
| Selectivity (%) | | | |
| $CF_3CF_2CH_3$ | 98.4 | | |
| $CHF_2CF_2CH_2F$ | | 1.1 | 61.3 |
| $CClF_2CF_2CH_3$ | | 88.1 | |
| $CHF_2CF_2CH_3$ | 0.9 | 10.1 | 34.1 |

EXAMPLE 4-27

The reaction was conducted and the reaction product was analyzed in the same manner as in Example 4-1 except that the hydrogenation catalyst prepared in the same manner as in Preparation Example 1 except that the catalyst component was platinum and the amount of supported catalyst was 1% by weight, was used, 1,1-dichloro-2,2,3,3,3-pentafluoropropane was used as the starting material and the reaction conditions as identified in Table 4-11 were employed. The results are shown in Table 4-11.

EXAMPLE 4-28

The reaction was conducted and the reaction product was analyzed in the same manner as in Example 4-1 except that the hydrogenation catalyst prepared in the same manner as in Preparation Example 2 except that the amount of the supported catalyst was 1% by weight, was used, 1,3-dichloro-1,1,2,2,3-pentafluoropropane was used as the starting material and the reaction conditions as shown in Table 4-11 were employed. The results are shown in Table 4-11.

EXAMPLE 4-29

The reaction was conducted and the reaction product was analyzed in the same manner as in Example 4-1 except that the hydrogenation catalyst prepared in the same manner as in Preparation Example 1 except that the catalyst component was platinum and the amount of the supported catalyst was 1% by weight, was used, 1,1-dichloro-1,2,2,3,3-pentafluoropropane was used as the starting material and the reaction conditions as identified in Table 4-11 were employed. The results are shown in Table 4-11.

TABLE 4-11

| Example No. | 4-27 | 4-28 | 4-29 |
|---|---|---|---|
| Catalyst | Pt | Pt | Pt |
| Support | Activated carbon | Activated carbon | Activated carbon |
| Reaction temp. (°C.) | 200 | 200 | 200 |
| Ratio of $H_2$/starting material (molar ratio) | 2 | 2 | 2 |
| Contact time (sec). | 20 | 20 | 20 |
| Conversion (%) | 99.9 | 99.9 | 99.9 |
| Selectivity (%) | | | |
| $CF_3CF_2CH_2Cl$ | 29.8 | | |
| $CF_3CF_2CH_3$ | 68.3 | | |
| $CClF_2CF_2CH_2F$ | | 40.7 | |
| $CHF_2CF_2CHClF$ | | 0.1 | 33.1 |
| $CHF_2CF_2CH_2F$ | | 0.1 | 58.1 |
| $CClF_2CF_2CH_3$ | | 56.1 | |
| $CHF_2CF_2CH_3$ | 0.5 | 1.4 | 7.9 |

EXAMPLE 4-30

The reaction was conducted and the reaction product was analyzed in the same manner as in Example 4-1 except that the hydrogenation catalyst prepared in the same manner as in Preparation Example 1 except that the catalyst component was platinum and the amount of supported catalyst was 1% by weight, was used, 1-chloro-2,2,3,3,3-pentafluoropropane was used as the starting material and the reaction conditions as identified in Table 4-12 were employed. The results are shown in Table 4-12.

EXAMPLE 4-31

The reaction was conducted and the reaction product was analyzed in the same manner as in Example 4-1 except that the hydrogenation catalyst prepared in the same manner as in Preparation Example 2 except that the amount of supported catalyst was 2% by weight, was used, 1-chloro-1,1,2,2,3-pentafluoropropane was used as the starting material and the reaction conditions as shown in Table 4-12 were employed. The results are shown in Table 4-12.

EXAMPLE 4-32

The reaction was conducted and the reaction product was analyzed in the same manner as in Example 4-1 except that the hydrogenation catalyst prepared in the same manner as in Preparation Example 1 except that the catalyst component was platinum and the amount of the supported catalyst was 2% by weight, was used, 1-chloro-1,2,2,3,3-pentafluoropropane was used as the starting material and the reaction conditions as identified in Table 4-12 were employed. The results are shown in Table 4-12.

TABLE 4-12

| Example No. | 4-30 | 4-31 | 4-32 |
|---|---|---|---|
| Catalyst | Pt | Pt | Pt |
| Support | Activated carbon | Activated carbon | Activated carbon |
| Reaction temp. (°C.) | 200 | 250 | 200 |
| Ratio of $H_2$/starting material (molar ratio) | 2 | 2 | 2 |
| Contact time (sec). | 20 | 30 | 20 |
| Conversion (%) | 99.9 | 89.6 | 99.9 |
| Selectivity (%) | | | |
| $CF_3CF_2CH_3$ | 99.3 | | |
| $CHF_2CF_2CH_2F$ | | 0.8 | 61.3 |
| $CClF_2CF_2CH_3$ | | 90.4 | |
| $CHF_2CF_2CH_3$ | 0.2 | 7.1 | 34.1 |

EXAMPLE 4-33

Into a 1 l SUS316 autoclave, 750 g of 1,1,3-trichloro-1,2,2,3,3-pentafluoropropane and 7.5 g of a platinum catalyst prepared in the same manner as in Preparation Example 2 except that the amount of the supported catalyst was 5% by weight and the support was activated carbon powder, were charged. A condenser was attached at the upper portion of the flange of the autoclave, and a valve was attached at the upper portion of the condenser to control the reaction pressure. The temperature of the cooling medium for the condenser was −20° C.

The interior of the autoclave was thoroughly replaced by nitrogen, and then the temperature was raised to 65° C. under stirring. Then, hydrogen was blown thereinto until the inner pressure became 2 kg/cm². Thereafter, hydrogen was introduced at a constant flow rate so that the inner pressure was maintained at a level of 2 kg/cm², and the temperature was maintained at about 60° C. The flow rate of the hydrogen at that time was 56 ml/min. The reaction gas which was not condensed by the condenser, was passed through water to remove hydrogen chloride and then passed through a trap cooled by dry ice, whereby the condensed product was collected.

Under such a state, the reaction was conducted for 120 hours under stirring. Then, the reaction solution was withdrawn, and the catalyst was separated by filtration. A mixture of the filtrate and the condensed product collected in the trap cooled by dry ice, was analyzed by gas chromatography. The results are shown in Table 4-13.

TABLE 4-13

| Conversion (%) | 71.0 |
|---|---|
| Selectivity (%) | |
| $CF_3CF_2CHCl_2$ | 45.3 |
| $CF_3CF_2CH_2Cl$ | 32.4 |

TABLE 4-13-continued

| Conversion (%) | 71.0 |
|---|---|
| $CF_3CF_2CH_3$ | 21.1 |

EXAMPLE 5-1

An Inconnel 600 reaction tube having an inner diameter of 2.54 cm and a length of 100 cm packed with 400 cc of a palladium catalyst supported on active carbon prepared in the same manner as in Preparation Example 1 was immersed in a salt bath furnace.

Hydrogen and starting material 1,1,3,3,3-pentachloro-2,2,3-trifluoropropane were gasified in a molar ratio of 3:1 and introduced into the reaction tube. The reaction temperature was 170° C., and the contact time was 20 seconds. After removing acid components, the reaction product was collected in a trap cooled to −78° C. The collected reaction product was analyzed by gas chromatography and by NMR. The results are shown in Table 5-1.

EXAMPLE 5-2

The hydrogenation reaction of 1,1,1,3,3-pentachloro-2,2,3-trifluoropropane was conducted and the reaction product was analyzed in the same manner as in Example 5-1 except that the hydrogenation catalyst prepared in the same manner as in Preparation Example 2 except that the catalyst component was palladium, was used and the reaction temperature was 220° C. The results are shown in Table 5-1.

EXAMPLE 5-3

The hydrogenation reaction of 1,1,1,3,3-pentachloro-2,2,3-trifluoropropane was conducted and the reaction product as analyzed in the same manner as in Example 5-1 except that the hydrogenation catalyst prepared in the same manner as in Preparation Example 2. The results are shown in Table 5-1.

TABLE 5-1

| Example No. | 5-1 | 5-2 | 5-3 |
|---|---|---|---|
| Catalyst | Pd | Pd | Pt |
| Reaction temp. (°C.) | 170 | 220 | 170 |
| Ratio of $H_2$/starting material (molar ratio) | 3 | 3 | 3 |
| Contact time (sec) | 20 | 20 | 20 |
| Conversion (%) | 99.9 | 99.9 | 84.1 |
| Selectivity (%) | | | |
| $CCl_2FCF_2CHCl_2$ | 6.3 | 5.7 | 21.3 |
| $CHClFCF_2CCl_3$ | 3.6 | 3.5 | 11.9 |
| $CCl_2FCF_2CH_2Cl$ | 33.2 | 33.0 | 27.6 |
| $CHClFCF_2CHCl_2$ | 0.9 | 0.8 | 3.1 |
| $CH_2FCF_2CCl_3$ | 4.1 | 4.5 | 3.6 |
| $CCl_2FCF_2CH_3$ | 28.1 | 27.1 | 24.1 |
| $CHClFCF_2CH_2Cl$ | 2.3 | 2.3 | 2.1 |
| $CH_2FCF_2CHCl_2$ | 12.1 | 13.1 | 3.7 |
| $CHClFCF_2CH_3$ | 1.9 | 2.0 | 0.7 |
| $CH_2FCF_2CH_2Cl$ | 4.8 | 4.4 | 0.4 |

EXAMPLES 5-4 TO 5-6

The hydrogenation reaction of 1,1,1,3,3-pentachloro-2,2,3-trifluoropropane was conducted and the reaction product was analyzed in the same manner as in Example 5-1 except that the reaction conditions as identified in Table 5-1 were employed and the hydrogenation catalyst to be used was prepared as follows. The hydrogenation catalyst was prepared in the same manner as in Preparation Example 1 except that the catalyst component was changed as shown in Table 5-2. The results are shown in Table 5-2.

TABLE 5-2

| Example No. | 5-4 | 5-5 | 5-6 |
|---|---|---|---|
| Catalyst | Pt | Ru | Rh |
| Reaction temp. (°C.) | 200 | 250 | 200 |
| Ratio of $H_2$/starting material (molar ratio) | 3 | 3 | 3 |
| Contact time (sec) | 20 | 20 | 20 |
| Conversion (%) | 97.9 | 56.3 | 84.3 |
| Selectivity (%) | | | |
| $CCl_2FCF_2CHCl_2$ | 21.0 | 0.1 | 17.0 |
| $CHClFCF_2CCl_3$ | 11.5 | 0.2 | 13.6 |
| $CCl_2FCF_2CH_2Cl$ | 28.3 | 0.2 | 27.1 |
| $CHClFCF_2CHCl_2$ | 3.0 | 0.1 | 1.5 |
| $CH_2FCF_2CCl_3$ | 3.1 | 0.6 | 1.7 |
| $CCl_2FCF_2CH_3$ | 24.3 | 57.1 | 29.3 |
| $CHClFCF_2CH_2Cl$ | 1.9 | 0.1 | 0.7 |
| $CH_2FCF_2CHCl_2$ | 4.1 | 0.1 | 1.6 |
| $CHClFCF_2CH_3$ | 0.7 | 0.2 | 0.1 |
| $CH_2FCF_2CH_2Cl$ | 0.4 | — | 0.4 |

EXAMPLES 5-7 AND 5-8

The hydrogenation reaction of 1,1,1,3,3-pentachloro-2,2,3-trifluoropropane was conducted and the reaction product was analyzed in the same manner as in Example 5-1 except that the reaction conditions as identified in Table 5-3 were employed and the hydrogenation catalyst to be used was prepared as follows. The hydrogenation catalyst was prepared in the same manner as in Preparation Example 2 except that the catalyst component was changed as shown in Table 5-3 and the reduction of the catalyst was carried out at 310° C. The results are shown in Table 5-3.

TABLE 5-3

| Example No. | 5-7 | 5-8 |
|---|---|---|
| Catalyst | Pd—Ni (8:2) | Pd—Co (9:1) |
| Reaction temp. (°C.) | 250 | 250 |
| Ratio of $H_2$/starting material (molar ratio) | 3 | 3 |
| Contact time (sec) | 20 | 20 |
| Conversion (%) | 86.7 | 87.6 |
| Selectivity (%) | | |
| $CCl_2FCF_2CHCl_2$ | 18.1 | 10.1 |
| $CHClFCF_2CCl_3$ | 12.5 | 11.3 |
| $CCl_2FCF_2CH_2Cl$ | 21.5 | 30.6 |
| $CHClFCF_2CHCl_2$ | 2.0 | 0.7 |
| $CH_2FCF_2CCl_3$ | 2.7 | 3.0 |
| $CCl_2FCF_2CH_3$ | 33.0 | 25.3 |
| $CHClFCF_2CH_2Cl$ | 0.6 | 2.1 |
| $CH_2FCF_2CHCl_2$ | 1.7 | 10.6 |
| $CHClFCF_2CH_3$ | 0.1 | 1.0 |
| $CH_2FCF_2CH_2Cl$ | 0.4 | 3.0 |

EXAMPLES 5-9 AND 5-10

The hydrogenation reaction of 1,1,1,3,3-pentachloro-2,2,3-trifluoropropane was conducted and the reaction product was analyzed in the same manner as in Example 5-1 except that the reaction conditions as identified in Table 5-4 were employed and the hydrogenation catalyst to be used was prepared as follows. The hydrogenation catalyst was prepared in the same manner as in Preparation Example 2 except that the catalyst component was changed as shown in Table 5-4 and the reduction of the catalyst was carried out at 320° C. The results are shown in Table 5-4.

TABLE 5-4

| Example No. | 5-9 | 5-10 |
|---|---|---|
| Catalyst | Pt—ReOx (1:1) | Pd—W (9:1) |
| Reaction temp. (°C.) | 250 | 260 |
| Ratio of $H_2$/starting material (molar ratio) | 3 | 3 |
| Contact time (sec) | 20 | 20 |
| Conversion (%) | 89.7 | 93.8 |
| Selectivity (%) | | |
| $CCl_2FCF_2CHCl_2$ | 17.1 | 5.6 |
| $CHClFCF_2CCl_3$ | 13.5 | 3.7 |
| $CCl_2FCF_2CH_2Cl$ | 26.5 | 27.0 |
| $CHClFCF_2CHCl_2$ | 1.5 | 0.9 |
| $CH_2FCF_2CCl_3$ | 1.8 | 4.4 |
| $CCl_2FCF_2CH_3$ | 28.1 | 28.1 |
| $CHClFCF_2CH_2Cl$ | 0.8 | 2.6 |
| $CH_2FCF_2CHCl_2$ | 1.9 | 11.6 |
| $CHClFCF_2CH_3$ | 0.1 | 2.0 |
| $CH_2FCF_2CH_2Cl$ | 0.4 | 5.6 |

EXAMPLES 5-11 TO 5-13

The hydrogenation reaction of 1,1,3,3-tetrachloro-1,2,2-trifluoropropane was conducted and the reaction product was analyzed in the same manner as in Example 5-1 except that the reaction conditions as identified in Table 5-5 were employed and the hydrogenation catalyst to be used was prepared as follows. The hydrogenation catalyst was prepared in the same manner as in Preparation Example 2 except that the catalyst component was changed as shown in Table 5-5, 2 wt % of the metal component was absorbed onto the activated carbon and the reduction of the catalyst was carried out at 230° C. The results are shown in Table 5-5.

TABLE 5-5

| Example No. | 5-11 | 5-12 | 5-13 |
|---|---|---|---|
| Catalyst | Pd | Pd | Pt |
| Reaction temp. (°C.) | 150 | 200 | 150 |
| Ratio of $H_2$/starting material (molar ratio) | 3 | 3 | 3 |
| Contact time (sec) | 20 | 20 | 20 |
| Conversion (%) | 80.3 | 99.9 | 70.9 |
| Selectivity (%) | | | |
| $CCl_2FCF_2CH_2Cl$ | 33.3 | 16.2 | 36.0 |
| $CHClFCF_2CHCl_2$ | 1.1 | 1.1 | 16.4 |
| $CCl_2FCF_2CH_3$ | 28.4 | 35.8 | 28.6 |
| $CHClFCF_2CH_2Cl$ | 2.3 | 2.3 | 3.7 |
| $CH_2FCF_2CHCl_2$ | 12.4 | 12.4 | 7.5 |
| $CHClFCF_2CH_3$ | 1.6 | 2.1 | 2.7 |
| $CH_2FCF_2CH_2Cl$ | 11.5 | 9.1 | 0.7 |
| $CH_3CF_2CHCl_2$ | 1.1 | 1.1 | 0.1 |
| $CH_2FCF_2CH_3$ | 2.7 | 7.1 | 1.5 |
| $CH_3CF_2CH_2Cl$ | 0.7 | 4.0 | 0.2 |

EXAMPLES 5-14 TO 5-16

The hydrogenation reaction of 1,1,3,3-tetrachloro-1,2,2-trifluoropropane was conducted and the reaction product was analyzed in the same manner as in Example 5-1 except that the reaction conditions as identified in Table 5-6 were employed and the hydrogenation catalyst to be used was prepared as follows. The hydrogenation catalyst was prepared in the same manner as in Preparation Example 1 except that the catalyst component was changed as shown in Table 5-6, 5 wt % of the metal component was absorbed onto the molded coconut shell activated carbon and the reduction of the catalyst was carried out by sodium borohydride. The results are shown in Table 5-6.

EXAMPLES 5-17 AND 5-18

The hydrogenation reaction of 1,1,3,3-tetrachloro-1,2,2-trifluoropropane was conducted and the reaction product was analyzed in the same manner as in Example 5-1 except that the reaction conditions as identified in Table 5-7 were employed and the hydrogenation catalyst to be used was prepared as follows. The hydrogenation catalyst was prepared in the same manner as in Preparation example 2 except that the catalyst component was changed as shown in Table 5-7, 5 wt % of the metal component was absorbed onto the molded coconut shell activated carbon and the reduction of the catalyst was carried out at 230° C. for 5 hours. The results are shown in Table 5-7.

TABLE 5-6

| Example No. | 5-14 | 5-15 | 5-16 |
|---|---|---|---|
| Catalyst | Pt | Ru | Rh |
| Reaction temp. (°C.) | 200 | 250 | 200 |
| Ratio of $H_2$/starting material (molar ratio) | 3 | 3 | 3 |
| Contact time (sec) | 20 | 20 | 20 |
| Conversion (%) | 99.9 | 65.3 | 75.6 |
| Selectivity (%) | | | |
| $CCl_2FCF_2CH_2Cl$ | 22.6 | 0.1 | 13.5 |
| $CHClFCF_2CHCl_2$ | 12.7 | 0.1 | 13.3 |
| $CCl_2FCF_2CH_3$ | 37.8 | 70.5 | 40.6 |
| $CHClFCF_2CH_2Cl$ | 5.3 | 0.1 | 3.5 |
| $CH_2FCF_2CHCl_2$ | 7.6 | 0.1 | 8.0 |
| $CHClFCF_2CH_3$ | 5.9 | 0.1 | 4.9 |
| $CH_2FCF_2CH_2Cl$ | 1.5 | — | 1.6 |
| $CH_3CF_2CHCl_2$ | 0.6 | — | 1.3 |
| $CH_2FCF_2CH_3$ | 1.7 | — | 0.1 |
| $CH_3CF_2CH_2Cl$ | 0.5 | — | 0.4 |

TABLE 5-7

| Example No. | 5-17 | 5-18 |
|---|---|---|
| Catalyst | Pd—Ni (7:3) | Pt—Co (9:1) |
| Reaction temp. (°C.) | 250 | 250 |
| Ratio of $H_2$/starting material (molar ratio) | 3 | 3 |
| Contact time (sec) | 20 | 20 |
| Conversion (%) | 87.5 | 88.0 |
| Selectivity (%) | | |
| $CCl_2FCF_2CH_2Cl$ | 16.3 | 18.3 |
| $CHClFCF_2CHCl_2$ | 4.0 | 3.6 |
| $CCl_2FCF_2CH_3$ | 37.1 | 30.5 |
| $CHClFCF_2CH_2Cl$ | 2.6 | 4.1 |
| $CH_2FCF_2CHCl_2$ | 13.1 | 6.1 |
| $CHClFCF_2CH_3$ | 2.1 | 4.8 |
| $CH_2FCF_2CH_2Cl$ | 8.1 | 1.5 |
| $CH_3CF_2CHCl_2$ | 2.3 | 0.6 |
| $CH_2FCF_2CH_3$ | 6.9 | 1.4 |
| $CH_3CF_2CH_2Cl$ | 3.5 | 1.0 |

EXAMPLE 5-19 AND 5-20

The hydrogenation reaction of 1,1,3,3-tetrachloro-1,2,2-trifluoropropane was conducted and the reaction product was analyzed in the same manner as in Example 5-1 except that the reaction conditions as identified in Table 5-8 were employed and the hydrogenation catalyst to be used was prepared as follows. The hydrogenation catalyst was prepared in the same manner as in Preparation Example 2 except that the catalyst component was changed as shown in Table 5-8, 2 wt % of the metal component was absorbed onto the activated carbon and the reduction of the catalyst was carried out at 290° C. The results are shown in Table 5-8.

TABLE 5-8

| Example No. | 5-19 | 5-20 |
|---|---|---|
| Catalyst | Pt—ReOx (1:1) | Pd—W (9:1) |
| Reaction temp. (°C.) | 250 | 250 |
| Ratio of $H_2$/starting material (molar ratio) | 3 | 3 |
| Contact time (sec) | 20 | 20 |
| Conversion (%) | 84.0 | 94.1 |
| Selectivity (%) | | |
| $CCl_2FCF_2CH_2Cl$ | 19.8 | 21.1 |
| $CHClFCF_2CHCl_2$ | 7.4 | 1.0 |
| $CCl_2FCF_2CH_3$ | 34.7 | 34.0 |
| $CHClFCF_2CH_2Cl$ | 3.0 | 2.1 |
| $CH_2FCF_2CHCl_2$ | 6.1 | 11.4 |
| $CHClFCF_2CH_3$ | 2.6 | 2.1 |
| $CH_2FCF_2CH_2Cl$ | 4.1 | 10.0 |
| $CH_3CF_2CHCl_2$ | 2.8 | 0.7 |
| $CH_2FCF_2CH_3$ | 5.1 | 6.5 |
| $CH_3CF_2CH_2Cl$ | 2.5 | 4.0 |

EXAMPLE 5-21

The hydrogenation reaction of 1,1,1,3-tetrachloro-2,2,3-trifluoropropane was conducted and the reaction product was analyzed in the same manner as in Example 5-1 except that the reaction conditions as identified in Table 5-9 were employed and the hydrogenation catalyst to be used was prepared as follows. The hydrogenation catalyst was prepared in the same manner as in Preparation Example 1 except that 5 wt % of the metal component was absorbed onto the activated carbon and the reduction of the catalyst was carried out by sodium borohydride. The result is shown in Table 5-9.

EXAMPLE 5-22

The hydrogenation reaction of 1,1,1-trichloro-2,2,3-trifluoropropane was conducted and the reaction product was analyzed in the same manner as in Example 5-1 except that the reaction conditions as identified in Table 5-9 were employed and the hydrogenation catalyst to be used was prepared in the same manner as in Example 5-21. The result is shown in Table 5-9.

EXAMPLE 5-23

The hydrogenation reaction of 1,1,3-trichloro-1,2,2-trifluoropropane was conducted and the reaction product was analyzed in the same manner as in Example 5-1 except that the reaction conditions as identified in Table 5-9 were employed and the hydrogenation catalyst to be used was prepared as follows. The hydrogenation catalyst was prepared in the same manner as in Preparation Example 1 except that 5 wt % of the metal component was absorbed onto the activated carbon and the reduction of the catalyst was carried out by sodium borohydride. The result is shown in Table 5-9.

TABLE 5-9

| Example No. | 5-21 | 5-22 | 5-23 |
|---|---|---|---|
| Catalyst | Pd | Pd | Pd |
| Reaction temp. (°C.) | 200 | 200 | 200 |
| Ratio of $H_2$/starting material (molar ratio) | 3 | 3 | 2 |
| Contact time (sec) | 20 | 20 | 20 |
| Conversion (%) | 99.9 | 99.9 | 88.9 |
| Selectivity (%) | | | |
| $CCl_3CF_2CH_2F$ | 15.6 | | |
| $CHCl_2CF_2CH_2F$ | 27.3 | 17.3 | |
| $CH_2ClCF_2CHClF$ | 0.3 | | 0.8 |
| $CH_2ClCF_2CH_2F$ | 21.6 | 35.4 | 35.3 |
| $CH_3CF_2CH_2F$ | 5.3 | 30.9 | 10.4 |
| $CCl_2FCF_2CH_3$ | | | 25.8 |
| $CHClFCF_2CH_3$ | | | 0.4 |

EXAMPLE 5-24

The reaction was conducted and the reaction product was analyzed in the same manner as in Example 5-1 except that 1,1,3-trichloro-2,2,3-trifluoropropane was used as the starting material and the reaction conditions as identified in Table 5-10 were employed. The results are shown in Table 5-10.

EXAMPLE 5-25

The reaction was conducted and the reaction product was analyzed in the same manner as in Example 5-1 except that 1,1-dichloro-1,2,2-trifluoropropane was used as the starting material and the reaction conditions as identified in Table 5-10 were employed. The results are shown in Table 5-10.

EXAMPLE 5-26

The reaction was conducted and the reaction product was analyzed in the same manner as in Example 5-1 except that 1,1-dichloro-2,2,3-trifluoropropane was used as the starting material and the reaction conditions as identified in Table 5-10 were employed. The results are shown in Table 5-10.

TABLE 5-10

| Example No. | 5-24 | 5-25 | 5-26 |
|---|---|---|---|
| Catalyst | Pd | Pd | Pd |
| Reaction temp. (°C.) | 200 | 200 | 200 |
| Ratio of $H_2$/starting material (molar ratio) | 2 | 2 | 2 |
| Contact time (sec) | 20 | 20 | 20 |
| Conversion (%) | 95.6 | 97.8 | 94.9 |
| Selectivity (%) | | | |
| $CHCl_2CF_2CH_2F$ | 20.8 | | |
| $CH_2ClCF_2CHClF$ | 1.6 | | |
| $CH_2ClCF_2CH_2F$ | 54.3 | | 20.5 |
| $CH_3CF_2CH_2F$ | 12.5 | 57.6 | 46.8 |
| $CHClFCF_2CH_3$ | | 15.8 | |

EXAMPLE 5-27

The reaction was conducted and the reaction product was analyzed in the same manner as in Example 5-1 except that 1,3-dichloro-1,2,2-trifluoropropane was used as the starting material and the reaction conditions as identified in Table 5-11 were employed. The results are shown in Table 5-11.

EXAMPLE 5-28

The reaction was conducted and the reaction product was analyzed in the same manner as in Example 5-1 except that 1-chloro-1,2,2-trifluoropropane was used as the starting material and the reaction conditions as identified in Table 5-11+were employed. The results are shown in Table 5-11.

EXAMPLE 5-29

The reaction was conducted and the reaction product was analyzed in the same manner as in Example 5-1 except that 1-chloro-2,2,3-trifluoropropane was used as the starting material and the reaction conditions as identified in Table 5-11 were employed. The results are shown in Table 5-11.

TABLE 5-11

| Example No. | 5-27 | 5-28 | 5-29 |
|---|---|---|---|
| Catalyst | Pd | Pd | Pd |
| Reaction temp. (°C.) | 200 | 200 | 200 |
| Ratio of $H_2$/starting material (molar ratio) | 2 | 2 | 2 |
| Contact time (sec) | 20 | 20 | 20 |
| Conversion (%) | 93.6 | 99.9 | 99.9 |
| Selectivity (%) | | | |
| $CH_2ClCF_2CH_2F$ | 16.5 | | |
| $CH_3CF_2CH_2F$ | 35.4 | 69.0 | 61.8 |
| $CHClFCF_2CH_3$ | 10.5 | | |

EXAMPLE 5-30

The reaction was conducted and the reaction product was analyzed in the same manner as in Example 5-1 except that as the hydrogenation catalyst, a platinum catalyst prepared in the same manner as in Preparation Example 2 except that the amount of supported catalyst was 2.0% by weight, was used, 1,1,1,3-tetrachloro-2,2,3-trifluoropropane was used as the starting material and the reaction conditions as identified in Table 5-12 were employed. The results are shown in Table 5-12.

EXAMPLE 5-31

The reaction was conducted and the reaction product was analyzed in the same manner as in Example 5-1 except that a platinum catalyst prepared in the same manner as in Example 5-30 was used, 1,1,1-trichloro-2,2,3-trifluoropropane was used as the starting material and the reaction conditions as shown in Table 5-12 were employed. The results are shown in Table 5-12.

EXAMPLE 5-32

The hydrogenation reaction of 1,1,3-trichloro-1,2,2-trifluoropropane was conducted and the reaction product was analyzed in the same manner as in Example 5-1 except that the reaction conditions as identified in Table 5-12 were employed and the hydrogenation catalyst to be used was prepared as follows. The hydrogenation catalyst was prepared in the same manner as in Preparation Example 2 except that 5 wt% of the metal component was absorbed onto the molded coconut shell activated carbon and the reduction of the catalyst was carried out at 235° C. for 6 hours. The results are shown in Table 5-12.

TABLE 5-12

| Example No. | 5-30 | 5-31 | 5-32 |
|---|---|---|---|
| Catalyst | Pt | Pt | Pt |
| Reaction temp. (°C.) | 200 | 200 | 200 |
| Ratio of $H_2$/starting material (molar ratio) | 3 | 3 | 2 |
| Contact time (sec) | 20 | 20 | 20 |
| Conversion (%) | 90.1 | 99.9 | 84.4 |
| Selectivity (%) | | | |
| $CCl_3CF_2CH_2F$ | 30.1 | | |
| $CHCl_2CF_2CH_2F$ | 20.4 | 25.3 | |
| $CH_2ClCF_2CHClF$ | 5.3 | | 15.9 |
| $CH_2ClCF_2CH_2F$ | 21.3 | 36.1 | 14.6 |
| $CH_3CF_2CH_2F$ | 0.7 | 25.6 | 14.0 |
| $CCl_2FCF_2CH_3$ | | | 30.4 |
| $CHClFCF_2CH_3$ | | | 7.3 |

EXAMPLE 5-33

The reaction was conducted and the reaction product was analyzed in the same manner as in Example 5-1 except that as the hydrogenation catalyst, a platinum catalyst prepared in the same manner as in Preparation Example 2 except that the amount of supported catalyst was 2.0% by weight, was used, 1,1,3-trichloro-2,2,3-trifluoropropane was used as the starting material and the reaction conditions as identified in Table 5-13 were employed. The results are shown in Table 5-13.

EXAMPLE 5-34

The hydrogenation reaction of 1,1-dichloro-1,2,2-trifluoropropane was conducted and the reaction product was analyzed in the same manner as in Example 5-1 except that the reaction conditions as identified in Table 5-13 were employed and the hydrogenation catalyst to be used was prepared as follows. The hydrogenation catalyst was prepared in the same manner as in Preparation Example 2 except that 5 wt % of the metal component was absorbed onto the molded coconut shell activated carbon and the reduction of the catalyst was carried out at 210° C. for 6 hours. The results are shown in Table 5-13.

EXAMPLE 5-35

The hydrogenation reaction of 1,1-dichloro-2,2,3-trifluoropropane was conducted and the reaction product was analyzed in the same manner as in Example 5-1 except that the reaction conditions as identified in Table 5-13 were employed and the hydrogenation catalyst to be used was prepared as follows. The hydrogenation catalyst was prepared in the same manner as in Preparation Example 1 except that the catalyst component was changed as shown in Table 5-13, 2 wt % of the metal component was absorbed onto the molded coconut shell activated carbon and the reduction of the catalyst was carried out by sodium borohydride. The results are shown in Table 5-13.

TABLE 5-13

| Example No. | 5-33 | 5-34 | 5-35 |
|---|---|---|---|
| Catalyst | Pt | Pt | Pt |
| Reaction temp. (°C.) | 200 | 200 | 200 |
| Ratio of $H_2$/starting material (molar ratio) | 2 | 2 | 2 |
| Contact time (sec) | 20 | 20 | 20 |
| Conversion (%) | 92.9 | 95.3 | 92.7 |
| Selectivity (%) | | | |
| $CHCl_2CF_2CH_2F$ | 23.9 | | |
| $CH_2ClCF_2CHClF$ | 3.5 | | |
| $CH_2ClCF_2CH_2F$ | 58.4 | | 32.5 |
| $CH_3CF_2CH_2F$ | 6.5 | 59.1 | 47.1 |
| $CHClFCF_2CH_3$ | | 31.6 | |

EXAMPLE 5-36

The reaction was conducted and the reaction product was analyzed in the same manner as in Example 5-1 except that a platinum catalyst prepared in the same manner as in Preparation Example 1 except that the amount of supported catalyst was 2% by weight, was used, 1,3-dichloro-1,2,2-trifluoropropane was used as the starting material and the reaction conditions as identified in Table 5-14 were employed. The results are shown in Table 5-14.

EXAMPLE 5-37

The reaction was conducted and the reaction product was analyzed in the same manner as in Example 5-1 except that as the hydrogenation catalyst, a platinum catalyst prepared in the same manner as in Preparation Example 2 except that the amount of supported catalyst was 2.0% by weight, was used, 1-chloro-1,1,2-trifluoropropane was used as the starting material and the reaction conditions as shown in Table 5-14 were employed. The results are shown in Table 5-14.

EXAMPLE 5-38

The reaction was conducted and the reaction product was analyzed in the same manner as in Example 5-1 except that the hydrogenation catalyst prepared in the same manner as in Example 5-37, was used, 1-chloro-2,2,3-trifluoropropane was used as-the starting material and the reaction conditions as identified in Table 5-14 were employed. The results are show in Table 5-14.

TABLE 5-14

| Example No. | 5-36 | 5-37 | 5-38 |
|---|---|---|---|
| Catalyst | Pt | Pt | Pt |
| Reaction temp. (°C.) | 200 | 200 | 200 |
| Ratio of $H_2$/starting material (molar ratio) | 2 | 2 | 2 |
| Contact time (sec) | 20 | 20 | 20 |
| Conversion (%) | 90.5 | 99.7 | 99.9 |
| Selectivity (%) | | | |
| $CH_2ClCF_2CH_2F$ | 25.4 | | |
| $CH_3CF_2CH_2F$ | 38.9 | 81.0 | 74.3 |
| $CHClFCF_2CH_3$ | 15.3 | | |

EXAMPLE 5-39

Into a 1 l SUS316 autoclave, 750 g of 1,1,3,3-tetrachloro-1,2,2-trifluoropropane and 7.5 g of a platinum catalyst prepared in the same manner as in Example 5-2 except that the amount of the supported catalyst was 5% by weight and the carrier was activated carbon powder, were charged. A condenser was attached at the upper portion of the flange of the autoclave, and a valve was attached at the upper portion of the condenser to control the reaction pressure. The temperature of the cooling medium for the condenser was −20° C.

The interior of the autoclave was thoroughly replaced by nitrogen, and then the temperature was raised to 65° C. under stirring. Then, hydrogen was blown thereinto until the inner pressure became 2 kg/cm². Thereafter, hydrogen was introduced at a constant flow rate so that the inner pressure was maintained at a level of 2 kg/cm² and the temperature was maintained at about 60° C. The flow rate of the hydrogen at that time was 560 ml/min. The reaction gas which was not condensed by the condenser, was passed through water to remove hydrogen chloride and then passed through a trap cooled by dry ice, whereby the condensed product was collected.

Under such a state, the reaction was conducted for 120 hours under stirring. Then, the reaction solution was withdrawn, and the catalyst was separated by filtration. A mixture of the filtrate and the condensed product collected in the trap cooled by dry ice, was analyzed by gas chromatography. The results are shown in Table 5-15.

TABLE 5-15

| | |
|---|---|
| Conversion (%) | 72.1 |
| Selectivity (%) | |
| $CCl_2FCF_2CH_2Cl$ | 34.1 |
| $CHClFCF_2CHCl_2$ | 18.5 |
| $CCl_2FCF_2CH_3$ | 28.1 |
| $CHClFCF_2CH_2Cl$ | 2.1 |
| $CH_2FCF_2CHCl_2$ | 5.1 |
| $CHClFCF_2CH_3$ | 2.7 |
| $CH_2FCF_2CH_2Cl$ | 0.7 |
| $CH_3CF_2CHCl_2$ | 0.1 |
| $CH_2FCF_2CH_3$ | 0.5 |
| $CH_3CF_2CH_2Cl$ | 0.2 |

EXAMPLE 6-1

An Inconnel 600 reaction tube having an inner diameter of 2.54 cm and a length of 100 cm packed with 40 cc of a palladium catalyst prepared in the same manner as in Preparation Example 1, was immersed in a salt bath furnace.

Hydrogen and starting material 1,1,3,3-tetrachloro-1,2,2,3-tetrafluoropropane were gasified in a molar ratio of 2:1 and introduced into the reaction tube. The reaction temperature was 200° C., and the contact time was 20 seconds. After removing acid components, the reaction product was collected in a trap cooled to −78° C. The collected reaction product was analyzed by gas chromatography and by NMR. The results are shown in Table 6-1.

EXAMPLES 6-2 AND 6-3

The hydrogenation reaction of 1,1,3,3-tetrachloro-1,2,2,3-tetrafluoropropane was conducted and the reaction product was analyzed in the same manner as in Example 6-1 except that the hydrogenation catalyst as identified in Table 6-1 which was prepared in the same manner as in Preparation Example 2 except that the catalyst component was changed as shown in Table 6-1, was used and the reaction conditions as identified in Table 6-1 were employed. The results are shown in Table 6-1.

TABLE 6-1

| Example No. | 6-1 | 6-2 | 6-3 |
|---|---|---|---|
| Catalyst | Pd | Pd | Pd |

TABLE 6-1-continued

| Example No. | 6-1 | 6-2 | 6-3 |
|---|---|---|---|
| Reaction temp. (°C.) | 200 | 200 | 200 |
| Ratio of H₂/starting material (molar ratio) | 2 | 3 | 2 |
| Contact time (sec) | 20 | 20 | 20 |
| Conversion (%) | 86.9 | 99.9 | 83.1 |
| Selectivity (%) | | | |
| $CCl_2FCF_2CHClF$ | 36.1 | 13.5 | 35.6 |
| $CHClFCF_2CHClF$ | 20.1 | 10.4 | 25.6 |
| $CCl_2FCF_2CH_2F$ | 24.2 | 25.4 | 22.2 |
| $CHClFCF_2CH_2F$ | 12.2 | 24.5 | 13.0 |
| $CCl_2FCF_2CH_3$ | 2.1 | 4.5 | 0.5 |
| $CH_2FCF_2CH_2F$ | 1.9 | 10.8 | 1.5 |
| $CHClFCF_2CH_3$ | 0.6 | 1.2 | 0.4 |
| $CH_2FCF_2CH_3$ | 1.8 | 4.4 | 0.5 |
| $CH_3CF_2CH_3$ | 0.7 | 5.0 | 0.4 |

EXAMPLES 6-4 TO 6-6

The hydrogenation reaction of 1,1,3,3-tetrachloro-1,2,2,3-tetrafluoropropane was conducted and the reaction product was analyzed in the same manner as in Example 6-1 except that the hydrogenation catalyst as identified in Table 6-2 which was prepared in the same manner as in Preparation Example 2 except that the catalyst component was changed as shown in Table 6-2, was used and the reaction conditions as identified in Table 6-2 were employed. The results are shown in Table 6-2.

TABLE 6-2

| Example No. | 6-4 | 6-5 | 6-6 |
|---|---|---|---|
| Catalyst | Pt | Ru | Rh |
| Reaction temp. (°C.) | 200 | 250 | 200 |
| Ratio of H₂/starting material (molar ratio) | 3 | 3 | 3 |
| Contact time (sec) | 20 | 20 | 20 |
| Conversion (%) | 99.0 | 66.3 | 85.3 |
| Selectivity (%) | | | |
| $CCl_2FCF_2CHClF$ | 25.1 | 3.8 | 14.1 |
| $CHClFCF_2CHClF$ | 22.6 | 4.1 | 15.1 |
| $CCl_2FCF_2CH_2F$ | 19.6 | 7.6 | 23.6 |
| $CHClFCF_2CH_2F$ | 17.4 | 3.6 | 16.6 |
| $CCl_2FCF_2CH_3$ | 2.5 | 35.1 | 18.7 |
| $CH_2FCF_2CH_2F$ | 8.1 | 13.6 | 2.1 |
| $CHClFCF_2CH_3$ | 0.7 | 17.6 | 7.1 |
| $CH_2FCF_2CH_3$ | 2.1 | 6.3 | 1.2 |
| $CH_3CF_2CH_3$ | 1.5 | 7.9 | 1.0 |

EXAMPLES 6-7 AND 6-8

The hydrogenation reaction of 1,1,3,3-tetrachloro-1,2,2,3-tetrafluoropropane was conducted and the reaction product was analyzed in the same manner as in Example 6-1 except that the hydrogenation catalyst as identified in Table 6-3 which was prepared in the same manner as in Preparation Example 2 except that the catalyst component was changed as shown in Table 6-3 and the reduction of the catalyst was carried out at 300° C., was used and the conditions for reduction as shown in Table 6-3 were employed. The results are shown in Table 6-3.

EXAMPLES 6-9 AND 6-10

The hydrogenation reaction of 1,1,3,3-tetrachloro-1,2,2,3-tetrafluoropropane was conducted and the reaction product was analyzed in the same manner as in Example 6-1 except that the hydrogenation catalyst as identified in Table 6-4 which was prepared in the same manner as in Preparation Example 2 except that the catalyst component was changed as shown in Table 6-4 and the reduction of the catalyst was carried out at 300° C., was used and the conditions for reduction as shown in Table 6-4 were employed. The results are shown in Table 6-4.

TABLE 6-3

| Example No. | 6-7 | 6-8 |
|---|---|---|
| Catalyst | Pd—Ni (8:2) | Pd—Co (9:1) |
| Reaction temp. (°C.) | 250 | 250 |
| Ratio of $H_2$/starting material (molar ratio) | 3 | 3 |
| Contact time (sec) | 20 | 20 |
| Conversion (%) | 86.3 | 89.6 |
| Selectivity (%) | | |
| $CCl_2FCF_2CHClF$ | 28.6 | 25.1 |
| $CHClFCF_2CHClF$ | 24.7 | 19.7 |
| $CCl_2FCF_2CH_2F$ | 23.7 | 22.4 |
| $CHClFCF_2CH_2F$ | 13.5 | 16.3 |
| $CCl_2FCF_2CH_3$ | 2.6 | 2.7 |
| $CH_2FCF_2CH_2F$ | 4.5 | 9.0 |
| $CHClFCF_2CH_3$ | 1.2 | 0.6 |
| $CH_2FCF_2CH_3$ | 1.7 | 2.1 |
| $CH_3CF_2CH_3$ | 0.2 | 1.8 |

TABLE 6-4

| Example No. | 6-9 | 6-10 |
|---|---|---|
| Catalyst | Pt—ReOx (1:1) | Pd—W (9:1) |
| Reaction temp. (°C.) | 250 | 250 |
| Ratio of $H_2$/starting material (molar ratio) | 3 | 3 |
| Contact time (sec) | 20 | 20 |
| Conversion (%) | 86.3 | 94.1 |
| Selectivity (%) | | |
| $CCl_2FCF_2CHClF$ | 24.6 | 13.4 |
| $CHClFCF_2CHClF$ | 21.6 | 10.2 |
| $CCl_2FCF_2CH_2F$ | 20.6 | 25.4 |
| $CHClFCF_2CH_2F$ | 17.4 | 24.1 |
| $CCl_2FCF_2CH_3$ | 3.0 | 4.7 |
| $CH_2FCF_2CH_2F$ | 7.6 | 10.8 |
| $CHClFCF_2CH_3$ | 1.1 | 1.3 |
| $CH_2FCF_2CH_3$ | 2.1 | 4.5 |
| $CH_3CF_2CH_3$ | 1.5 | 4.9 |

EXAMPLES 6-11 TO 6-13

The hydrogenation reaction of 1,1,3-trichloro-2,2,3,3-tetrafluoropropane was conducted and the reaction product was analyzed in the same manner as in Example 6-1 except that the hydrogenation catalyst as identified in Table 6-5 which was prepared in the same manner as in Preparation Example 2 except that the catalyst component was changed as shown in Table 6-5 and the reduction of the catalyst was carried out at 250° C., was used and the conditions for reduction as shown in Table 6-5 were employed. The results are shown in Table 6-5.

EXAMPLES 6-14 TO 6-16

The hydrogenation reaction of 1,1,3-trichloro-2,2,3,3-tetrafluoropropane was conducted and the reaction product was analyzed in the same manner as in Example 6-1 except that the hydrogenation catalyst as identified in Table 6-6 which was prepared in the same manner as in Preparation Example 2 except that the catalyst component was changed as shown in Table 6-6 and the reduction of the catalyst was carried out at 250° C., was used and the conditions for reduction as shown in Table 6-6 were employed. The results are shown in Table 6-6.

TABLE 6-5

| Example No. | 6-11 | 6-12 | 6-13 |
|---|---|---|---|
| Catalyst | Pd | Pd | Pt |
| Reaction temp. (°C.) | 200 | 200 | 200 |
| Ratio of $H_2$/starting material (molar ratio) | 2 | 3 | 2 |
| Contact time (sec) | 20 | 20 | 20 |
| Conversion (%) | 86.4 | 99.9 | 74.6 |
| Selectivity (%) | | | |
| $CClF_2CF_2CH_2Cl$ | 67.1 | 55.3 | 71.6 |
| $CClF_2CF_2CH_3$ | 31.4 | 43.7 | 26.5 |
| $CHF_2CF_2CH_3$ | 0.3 | 0.3 | 0.3 |

TABLE 6-6

| Example No. | 6-14 | 6-15 | 6-16 |
|---|---|---|---|
| Catalyst | Pt | Ru | Rh |
| Reaction temp. (°C.) | 200 | 250 | 250 |
| Ratio of $H_2$/starting material (molar ratio) | 3 | 3 | 3 |
| Contact time (sec) | 20 | 20 | 20 |
| Conversion (%) | 99.9 | 75.1 | 95.3 |
| Selectivity (%) | | | |
| $CClF_2CF_2CH_2Cl$ | 56.3 | 43.7 | 45.3 |
| $CClF_2CF_2CH_3$ | 42.0 | 56.3 | 51.0 |
| $CHF_2CF_2CH_3$ | 0.3 | — | 0.1 |

EXAMPLES 6-17 AND 6-18

The hydrogenation reaction of 1,1,3-trichloro-2,2,3,3-tetrafluoropropane was conducted and the reaction product was analyzed in the same manner as in Example 6-1 except that the hydrogenation catalyst as identified in Table 6-7 which was prepared in the same manner as in Preparation Example 2 except that the catalyst component was changed as shown in Table 6-7 and the reduction of the catalyst was carried out at 300° C., was used and the conditions for reduction as shown in Table 6-7 were employed. The results are shown in Table 6-7.

EXAMPLES 6-19 AND 6-20

The hydrogenation reaction of 1,1,3-trichloro-2,2,3,3-tetrafluoropropane was conducted and the reaction product was analyzed in the same manner as in Example 6-1 except that the hydrogenation catalyst prepared in the same manner as in Preparation Example 4 except that the catalyst component was changed as shown in Table 6-8, was used and conditions for reduction as shown in Table 6-8 were employed. The results are shown in Table 6-8.

TABLE 6-7

| Example No. | 6-17 | 6-18 |
|---|---|---|
| Catalyst | Pd—Ni (8:2) | Pt—Co (9:1) |
| Reaction temp. (°C.) | 250 | 250 |
| Ratio of $H_2$/starting material (molar ratio) | 3 | 3 |
| Contact time (sec) | 20 | 20 |
| Conversion (%) | 92.5 | 91.0 |

TABLE 6-7-continued

| Example No. | 6-17 | 6-18 |
|---|---|---|
| Selectivity (%) | | |
| $CClF_2CF_2CH_2Cl$ | 50.4 | 52.5 |
| $CClF_2CF_2CH_3$ | 48.5 | 46.8 |
| $CHF_2CF_2CH_3$ | 0.1 | 0.1 |

TABLE 6-8

| Example No. | 6-19 | 6-20 |
|---|---|---|
| Catalyst | Pt—Re (1:1) | Pd—W (9:1) |
| Reaction temp. (°C.) | 250 | 250 |
| Ratio of $H_2$/starting material (molar ratio) | 3 | 3 |
| Contact time (sec) | 20 | 20 |
| Conversion (%) | 97.0 | 87.0 |
| Selectivity (%) | | |
| $CClF_2CF_2CH_2Cl$ | 40.8 | 43.3 |
| $CClF_2CF_2CH_3$ | 58.5 | 55.8 |
| $CHF_2CF_2CH_3$ | 0.1 | 0.3 |

EXAMPLE 6-21

The reaction was conducted and the reaction product was analyzed in the same manner as in Example 6-1 except that 1,1,1,3-tetrachloro-2,2,3,3-tetrafluoropropane was used as the starting material and the reaction conditions as identified in Table 6-9 were employed. The results are shown in Table 6-9.

EXAMPLE 6-22

The reaction was conducted and the reaction product was analyzed in the same manner as in Example 6-1 except that 1,1,3-trichloro-1,2,2,3-tetrafluoropropane was used as the starting material and the reaction conditions as identified in Table 6-9 were employed. The results are shown in Table 6-9.

EXAMPLE 6-23

The reaction was conducted and the reaction product was analyzed in the same manner as in Example 6-1 except that 1,1,1-trichloro-2,2,3,3-tetrafluoropropane was used as the starting material and the reaction conditions as identified in Table 6-9 were employed. The results are shown in Table 6-9.

TABLE 6-9

| Example No. | 6-21 | 6-22 | 6-23 |
|---|---|---|---|
| Catalyst | Pd | Pd | Pd |
| Reaction temp. (°C.) | 200 | 200 | 200 |
| Ratio of $H_2$/starting material (molar ratio) | 3 | 3 | 2 |
| Contact time (sec) | 20 | 20 | 20 |
| Conversion (%) | 99.9 | 99.9 | 98.9 |
| Selectivity (%) | | | |
| $CClF_2CF_2CHCl_2$ | 18.9 | | |
| $CClF_2CF_2CH_2Cl$ | 34.7 | | |
| $CClF_2CF_2CH_3$ | 42.1 | | |
| $CCl_2FCF_2CH_2F$ | | 18.9 | |
| $CHClFCF_2CHClF$ | | 2.4 | |
| $CHClFCF_2CH_2F$ | | 6.6 | |
| $CCl_2FCF_2CH_3$ | | 4.7 | |

TABLE 6-9-continued

| Example No. | 6-21 | 6-22 | 6-23 |
|---|---|---|---|
| $CH_2FCF_2CH_2F$ | | 47.3 | |
| $CHCl_2CF_2CHF_2$ | | | 22.7 |
| $CH_2ClCF_2CHF_2$ | | | 36.1 |
| $CH_3CF_2CHF_2$ | | | 39.7 |

EXAMPLE 6-24

The reaction was conducted and the reaction product was analyzed in the same manner as in Example 6-1 except that 1,3-dichloro-1,2,2,3-tetrafluoropropane was used as the starting material and the reaction conditions as identified in Table 6-10 were employed. The results are shown in Table 6-10.

EXAMPLE 6-25

The reaction was conducted and the reaction product was analyzed in the same manner as in Example 6-1 except that 1,1-dichloro-2,2,3,3-tetrafluoropropane was used as the starting material and the reaction conditions as identified in Table 6-10 were employed. The results are shown in Table 6-10.

TABLE 6-10

| Example No. | 6-24 | 6-25 |
|---|---|---|
| Catalyst | Pd | Pd |
| Reaction temp. (°C.) | 200 | 200 |
| Ratio of $H_2$/starting material (molar ratio) | 2 | 2 |
| Contact time (sec) | 20 | 20 |
| Conversion (%) | 96.9 | 99.8 |
| Selectivity (%) | | |
| $CHClFCF_2CH_2F$ | 31.9 | |
| $CH_2FCF_2CH_2F$ | 58.9 | |
| $CHClFCF_2CH_3$ | 1.2 | |
| $CH_2FCF_2CH_3$ | 3.6 | |
| $CH_2ClCF_2CHF_2$ | | 21.3 |
| $CH_3CF_2CHF_2$ | | 77.5 |
| $CH_3CF_2CH_3$ | 2.0 | |

EXAMPLE 6-26

The reaction was conducted and the reaction product was analyzed in the same manner as in Example 6-1 except that 1,3-dichloro-1,1,2,2-tetrafluoropropane was used as the starting material and the reaction conditions as identified in Table 6-11 were employed. The results are shown in Table 6-11.

EXAMPLE 6-27

The reaction was conducted and the reaction product was analyzed in the same manner as in Example 6-1 except that 1,1-dichloro-1,2,2,3-tetrafluoropropane was used as the starting material and the reaction conditions as identified in Table 6-11 were employed. The results are shown in Table 6-11.

EXAMPLE 6-28

The reaction was conducted End the reaction product was analyzed in the same manner as in Example 6-1 except that 1-chloro-2,2,3,3-tetrafluoropropane was used as the starting material and the reaction conditions as identified in Table 6-11 were employed. The results are shown in Table 6-11.

TABLE 6-11

| Example No. | 6-26 | 6-27 | 6-28 |
|---|---|---|---|
| Catalyst | Pd | Pd | Pd |
| Reaction temp. (°C.) | 200 | 200 | 200 |
| Ratio of $H_2$/starting material (molar ratio) | 2 | 2 | 2 |
| Contact time (sec) | 20 | 20 | 20 |
| Conversion (%) | 99.9 | 95.9 | 99.9 |
| Selectivity | | | |
| $CClF_2CF_2CH_3$ | 96.2 | | |
| $CHClFCF_2CH_2F$ | | 4.1 | |
| $CCl_2FCF_2CH_3$ | | 2.0 | |
| $CH_2FCF_2CH_2F$ | | 57.0 | |
| $CH_2FCF_2CH_3$ | | 21.0 | |
| $CHCl_2CF_2CHF_2$ | | 0.7 | |
| $CH_3CF_2CHF_2$ | 1.9 | | 95.0 |

EXAMPLE 6-29

The reaction was conducted and the reaction product was analyzed in the same manner as in Example 6-1 except that 1-chloro-1,2,2,3-tetrafluoropropane was used as the starting material and the reaction conditions as identified in Table 6-12 were employed. The results are shown in Table 6-12.

EXAMPLES 6-30

The reaction was conducted and the reaction product was analyzed in the same manner as in Example 6-1 except that 1-chloro-1,1,2,2-tetrafluoropropane was used as the starting material and the reaction conditions as identified in Table 6-12 were employed. The results are shown in Table 6-12.

TABLE 6-12

| Example No. | 6-29 | 6-30 |
|---|---|---|
| Catalyst | Pd | Pd |
| Reaction temp. (°C.) | 250 | 200 |
| Ratio of $H_2$/starting material (molar ratio) | 2 | 2 |
| Contact time (sec) | 20 | 30 |
| Conversion (%) | 93.5 | 76.2 |
| Selectivity (%) | | |
| $CH_2FCF_2CH_2F$ | 18.9 | |
| $CHClFCF_2CH_3$ | 0.7 | |
| $CH_2FCF_2CH_3$ | 54.1 | |
| $CH_2ClCF_2CHF_2$ | | 68.9 |
| $CH_3CF_2CH_3$ | 18.8 | |

EXAMPLE 6-31

The reaction was conducted and the reaction product was analyzed in the same manner as in Example 6-1 except that as the hydrogenation catalyst, a platinum catalyst prepared in the same manner as in Preparation Example 2, was used, 1,1,1,3-tetrachloro-2,2,3,3-tetrafluoropropane was used as the starting material and the reaction conditions as identified in Table 6-13 were employed. The results are shown in Table 6-13.

EXAMPLE 6-32

The reaction was conducted and the reaction product was analyzed in the same manner as in Example 6-1 except that as the hydrogenation catalyst, a platinum catalyst prepared in the same manner as in Preparation Example 2 was used, 1,1,3-trichloro-1,2,2,3-tetrafluoropropane was used as the starting material and the reaction conditions as shown in Table 6-13 were employed. The results are shown in Table 6-13.

EXAMPLE 6-33

The reaction was conducted and the reaction product was analyzed in the same manner as in Example 6-1 except that as the hydrogenation catalyst, a platinum catalyst prepared in the same manner as in Preparation Example 2 was used, 1,1,1-trichloro-2,2,3,3-tetrafluoropropane was used as the starting material and the reaction conditions as identified in Table 6-13 were employed. The results are shown in Table 6-13.

TABLE 6-13

| Example No. | 6-31 | 6-32 | 6-33 |
|---|---|---|---|
| Catalyst | Pt | Pt | Pt |
| Reaction temp. (°C.) | 200 | 200 | 200 |
| Ratio of $H_2$/starting material (molar ratio) | 3 | 3 | 2 |
| Contact time (sec) | 20 | 20 | 20 |
| Conversion (%) | 99.0 | 99.9 | 90.9 |
| Selectivity (%) | | | |
| $CClF_2CF_2CHCl_2$ | 17.6 | | |
| $CClF_2CF_2CH_2Cl$ | 26.7 | | |
| $CClF_2CF_2CH_3$ | 52.1 | | |
| $CCl_2FCF_2CH_2F$ | | 16.3 | |
| $CHClFCF_2CHClF$ | | 6.5 | |
| $CHClFCF_2CH_2F$ | | 4.9 | |
| $CCl_2FCF_2CH_3$ | | 15.4 | |
| $CH_2FCF_2CH_2F$ | | 50.8 | |
| $CHCl_2CF_2CHF_2$ | | | 30.1 |
| $CH_2ClCF_2CHF_2$ | | | 37.4 |
| $CH_3CF_2CHF_2$ | | | 31.3 |

EXAMPLE 6-34

The reaction was conducted and the reaction product was analyzed in the same manner as in Example 6-1 except that as the hydrogenation catalyst, a platinum catalyst prepared in the same manner as in Preparation Example 2 was used, 1,3-dichloro-1,2,2,3-tetrafluoropropane was used as the starting material and the reaction conditions as identified in Table 6-14 were employed. The results are shown in Table 6-14.

EXAMPLE 6-35

The reaction was conducted and the reaction product was analyzed in the same manner as in Example 6-1 except that as the hydrogenation catalyst, a platinum catalyst prepared in the same manner as in Preparation Example 2 was used, 1,1-dichloro-2,2,3,3-tetrafluoropropane was used as the starting material and the reaction conditions as shown in Table 6-14 were employed. The results are shown in Table 6-14.

TABLE 6-14

| Example No. | 6-34 | 6-35 |
|---|---|---|
| Catalyst | Pt | Pt |
| Reaction temp. (°C.) | 200 | 200 |
| Ratio of $H_2$/starting material (molar ratio) | 2 | 2 |
| Contact time (sec) | 20 | 20 |
| Conversion (%) | 95.3 | 99.9 |
| Selectivity (%) | | |
| $CHClFCF_2CH_2F$ | 40.0 | |
| $CH_2FCF_2CH_2F$ | 55.1 | |

TABLE 6-14-continued

| Example No. | 6-34 | 6-35 |
|---|---|---|
| CHClFCF$_2$CH$_3$ | 0.3 | |
| CH$_2$FCF$_2$CH$_3$ | 0.6 | |
| CH$_2$ClCF$_2$CHF$_2$ | | 30.9 |
| CH$_3$CF$_2$CHF$_2$ | | 66.9 |
| CH$_3$CF$_2$CH$_3$ | 0.4 | |

EXAMPLE 6-36

The reaction was conducted and the reaction product was analyzed in the same manner as in Example 6-1 except that as the hydrogenation catalyst, a platinum catalyst prepared in the same manner as in Preparation Example 2 was used, 1,3-dichloro-1,1,2,2-tetrafluoropropane was used as the starting material and the reaction conditions as identified in Table 6-15 were employed. The results are shown in Table 6-15.

EXAMPLE 6-37

The reaction was conducted and the reaction product was analyzed in the same manner as in Example 6-1 except that as the hydrogenation catalyst, a platinum catalyst prepared in the same manner as in Preparation Example 2 was used, 1,1-dichloro-1,2,2,3-tetrafluoropropane was used as the starting material and the reaction conditions as shown in Table 6-15 were employed. The results are shown in Table 6-15.

EXAMPLE 6-38

The reaction was conducted and the reaction product was analyzed in the same manner as in Example 6-1 except that as the hydrogenation catalyst, a platinum catalyst prepared in the same manner as in Preparation Example 2, was used, 1-chloro-2,2,3,3-tetrafluoropropane was used as the starting material and the reaction conditions as identified in Table 6-15 were employed. The results are shown in Table 6-15.

TABLE 6-15

| Example No. | 6-36 | 6-37 | 6-38 |
|---|---|---|---|
| Catalyst | Pt | Pt | Pt |
| Reaction temp. (°C.) | 200 | 200 | 200 |
| Ratio of H$_2$/starting material (molar ratio) | 2 | 2 | 2 |
| Contact time (sec) | 20 | 20 | 20 |
| Conversion (%) | 99.9 | 91.4 | 99.9 |
| Selectivity (%) | | | |
| CClF$_2$CF$_2$CH$_3$ | 96.9 | | |
| CHClFCF$_2$CH$_2$F | | 23.2 | |
| CCl$_2$FCF$_2$CH$_3$ | | 1.5 | |
| CH$_2$FCF$_2$CH$_2$F | | 46.4 | |
| CH$_2$FCF$_2$CH$_3$ | | 10.8 | |
| CHCl$_2$CF$_2$CHF$_2$ | | 3.1 | |
| CH$_3$CF$_2$CHF$_2$ | 1.0 | | 96.4 |

EXAMPLE 6-39

The reaction was conducted and the reaction product was analyzed in the same manner as in Example 6-1 except that as the hydrogenation catalyst, a platinum catalyst prepared in the same manner as in Preparation Example 2 was used, 1-chloro-1,2,2,3-tetrafluoropropane was used as the starting material and the reaction conditions as identified in Table 6-16 were employed. The results are shown in Table 6-16.

EXAMPLE 6-40

The reaction was conducted and the reaction product was analyzed in the same manner as in Example 6-1 except that as the hydrogenation catalyst, a platinum catalyst prepared in the same manner as in Preparation Example 2 was used, 1-chloro-1,1,2,2-tetrafluoropropane was used as the starting material and the reaction conditions as shown in Table 6-16 were employed. The results are shown in Table 6-16.

TABLE 6-16

| Example No. | 6-39 | 6-40 |
|---|---|---|
| Catalyst | Pt | Pt |
| Reaction temp. (°C.) | 250 | 200 |
| Ratio of H$_2$/starting material (molar ratio) | 2 | 2 |
| Contact time (sec) | 20 | 30 |
| Conversion (%) | 91.2 | 66.2 |
| Selectivity (%) | | |
| CH$_2$FCF$_2$CH$_2$F | 20.7 | |
| CHClFCF$_2$CH$_3$ | 7.9 | |
| CH$_2$FCF$_2$CH$_3$ | 56.4 | |
| CH$_2$ClCF$_2$CHF$_2$ | | 76.5 |
| CH$_3$CF$_2$CH$_3$ | 10.2 | |

EXAMPLE 6-41

Into a 1 l SUS316 autoclave, 750 g of 1,1,1,3-tetrachloro-2,2,3,3-tetrafluoropropane and 7.5 g of a platinum catalyst prepared in the same manner as in Preparation Example 2 except that the catalyst component was platinum, the support was activated carbon powder and the amount of supported catalyst was 5% by weight were charged. A condenser was attached at the upper portion of the flange of the autoclave, and a valve was attached at the upper portion of the condenser to control the reaction pressure. The temperature of the cooling medium for the condenser was −20° C.

The inside of the autoclave was thoroughly replaced by nitrogen, and then the temperature was raised to 65° C. under stirring. Then, hydrogen was blown thereinto until the inner pressure became 2 kg/cm$^2$. Thereafter, hydrogen was introduced at a constant flow rate so that the inner pressure was maintained at a level of 2 kg/cm$^2$, and the temperature was maintained at about 60° C. The flow rate of the hydrogen at that time was 56 ml/min. The reaction gas which was not condensed by the condenser, was passed through water to remove hydrogen chloride and then passed through a trap cooled by dry ice, whereby the condensed product was collected.

Under such a state, the reaction was conducted for 120 hours under stirring. Then, the reaction solution was withdrawn, and the catalyst was separated by filtration. A mixture of the filtrate and the condensed product collected in the trap cooled by dry ice, was analyzed by gas chromatography. The results are shown in Table 6-17.

TABLE 6-17

| Conversion (%) | 78.9 |
|---|---|
| Selectivity (%) | |
| CClF$_2$CF$_2$CH$_2$Cl | 54.1 |
| CClF$_2$CF$_2$CH$_3$ | 44.8 |

The present invention is effective for producing a hydrogen-containing 2,2-difluoropropane selectively by subjecting 2,2-difluoropropane to hydrogen reduction.

We claim:

1. A process for producing a hydrogen-containing 2,2-difluoropropane of the following formula (2), which comprises subjecting a 2,2-difluoropropane of the following formula (1) to hydrogen reduction at a temperature of from 100° to 450° C. wherein the hydrogen reduction is conducted in a gas phase by hydrogen in the presence of a platinum group metal catalyst which contains at least one metal selected from the group consisting of Pt, Pd, Rh and Ru, $$C_3H_aCl_bF_c \qquad (1)$$

$$C_3H_{a+x}Cl_{b-y}F_{c-z} \qquad (2)$$

wherein a, b, c, x, y and z are integers satisfying the following conditions:
$a \geq 0$, $4 \geq b \geq 1$, $6 \geq c \geq 2$, $x \geq 1$, $y \geq 1$, $z \geq 0$, $a+b+c=8$, $x=y+z$ $b-y=0$, and $c-z \geq 2$.

2. The process according to claim 1, wherein the platinum group metal catalyst is a platinum group metal catalyst supported on activated carbon.

* * * * *